US011684240B2

(12) United States Patent
Orth

(10) Patent No.: US 11,684,240 B2
(45) Date of Patent: Jun. 27, 2023

(54) MULTICORE FIBER IMAGING

(71) Applicant: ROYAL MELBOURNE INSTITUTE OF TECHNOLOGY, Melbourne (AU)

(72) Inventor: Antony Orth, Melbourne (AU)

(73) Assignee: ROYAL MELBOURNE INSTITUTE OF TECHNOLOGY, Melbourne (AU)

( * ) Notice: Subject to any disclaimer, the term of this patent is extended or adjusted under 35 U.S.C. 154(b) by 126 days.

(21) Appl. No.: 16/965,513

(22) PCT Filed: Jan. 25, 2019

(86) PCT No.: PCT/AU2019/050055
§ 371 (c)(1),
(2) Date: Jul. 28, 2020

(87) PCT Pub. No.: WO2019/144194
PCT Pub. Date: Aug. 1, 2019

(65) Prior Publication Data
US 2021/0048660 A1 Feb. 18, 2021

(30) Foreign Application Priority Data

Jan. 29, 2018 (AU) .............................. 2018900267

(51) Int. Cl.
*G02B 6/02* (2006.01)
*A61B 1/00* (2006.01)
(Continued)

(52) U.S. Cl.
CPC .... *A61B 1/000095* (2022.02); *A61B 1/00194* (2022.02); *G02B 6/02042* (2013.01);
(Continued)

(58) Field of Classification Search
None
See application file for complete search history.

(56) References Cited

U.S. PATENT DOCUMENTS 5,751,340 A    5/1998  Strobl et al.
8,811,769 B1   8/2014  Pitts et al.
(Continued)

FOREIGN PATENT DOCUMENTS

JP    H04138127 A    5/1992
JP    H09218940 A    8/1997
(Continued)

OTHER PUBLICATIONS

International Search Report and Written Opinion dated Apr. 10, 2019 for International Application No. PCT/AU2019/050055.
(Continued)

*Primary Examiner* — Chad H Smith
(74) *Attorney, Agent, or Firm* — David F. Dockery; The Navitas Intellectual Property Group LLC

(57) ABSTRACT

The invention relates to multicore fiber imaging, such as used in endoscopy. Methods are described for processing images captured with such systems to achieve an improved depth of field image or extract 3D information concerning the images, without requiring the addition of additional optical components. One method for generating an image from light received by an imager via a multiplicity of waveguides includes receiving a digital image containing a plurality of pixels, the digital image including a plurality of regions within it wherein each of said regions corresponds to a waveguide core. Each region includes a plurality of pixels, and a first subset of pixels within each region is defined which at least partly correlates with light having been received at a corresponding core in a first spatial arrangement, the subset including less than all of the pixels within a region. A first image is generated from the first subset of pixels from said regions, combined to form an image over the whole waveguide array. The first spatial arrangement may correspond to a measure of angular dimension of the (Continued)

incident light for that region. In addition to increased depth of field, the modified images provided by the invention allow 3D visualisation of objects, eg. using stereographs or depth mapping techniques.

7 Claims, 9 Drawing Sheets

(51) Int. Cl.
*G06T 7/557* (2017.01)
*G02B 6/06* (2006.01)
*G02B 23/26* (2006.01)
*G06T 5/50* (2006.01)

(52) U.S. Cl.
CPC ............. *G02B 6/065* (2013.01); *G02B 23/26* (2013.01); *G06T 5/50* (2013.01); *G06T 7/557* (2017.01); *G06T 2207/10052* (2013.01); *G06T 2207/10068* (2013.01); *G06T 2207/20216* (2013.01)

(56) References Cited

U.S. PATENT DOCUMENTS

| | | |
|---|---|---|
| 2002/0159728 A1 | 10/2002 | Kobayashi et al. |
| 2017/0243373 A1 | 8/2017 | Bevensee et al. |
| 2017/0365068 A1 | 12/2017 | Tan et al. |

FOREIGN PATENT DOCUMENTS

| | | |
|---|---|---|
| JP | 2013192063 A | 9/2013 |
| TW | I594628 B | 8/2017 |

OTHER PUBLICATIONS

Orth, A et al, "Extended Depth of Field Imaging Through Multicore Optical Fibers" Optics Express 6407, vol. 26, No. 5. Published Mar. 5, 2018.

Extended European Search Report dated Apr. 7, 2022 for EP Application No. 19743938.3.

Office Action for Japanese Patent Application No. 2020-541380 dated Dec. 20, 2022.

MULTICORE FIBER IMAGING

FIELD OF THE INVENTION

The present invention relates primarily to multicore fiber imaging, such as used in endoscopy. In preferred forms methods are described for processing images captured with such systems to achieve an improved depth of field image or extract 3D information concerning the images, without requiring the addition of additional optical components.

BACKGROUND OF THE INVENTION

Multicore optical fibers (MOFs) are widely used as microendoscopic probes for imaging inside the body. Such MOFs contain thousands of waveguide cores, each 2-3 μm in diameter that relay light from inside the body to an imager that operates as an external detector. The imager generates an image of the distal end of the MOF. The image generated contains a plurality of pixels and includes a plurality of regions within it that each correspond to a waveguide core. Each core will be imaged over a plurality of pixels in the image. The digital image will also include pixels that correspond to interstitial space between said waveguide cores. FIG. 1 illustrates a portion of such an image. In FIG. 1 the contiguous black image portion 2 corresponds to pixels imaging the interstitial space between wave guide cores. The lighter regions (e.g. 4) of varying grey levels correspond to individual waveguide cores, the level of illumination thereof corresponding to the light received at the distal facet of each fiber.

Developments in MOF techniques have included processing of received data to improve image quality, including filtering techniques to deal with image artefact produced by the interstitial regions between the fiber cores, that can otherwise render as distracting patterns such as visible grids or Moiré effects. U.S. Pat. No. 5,751,340, for example, discloses reducing the contrast of the grid pattern components by suitable filtering, such as the applying a dilation process to interpolate from the brighter center of each fiber into the neighbourhood interstitial regions.

Multicore optical fibers enable a wide variety of microendoscopic imaging modes, including optical coherence tomography, reflectance and fluorescence (confocal, widefield, and multiphoton).

When equipped with a microlens on the distal facet, MOFs operate at a small working distance, typically on the order of 50-100 μm. Imaging is also possible in contact mode, where the bare fiber facet is directly in contact with the sample. In this case, the Nyquist-limited resolution is twice the core-to-core distance, whereas in lensed systems, the resolution is scaled by the inverse magnification.

In both lensless and lensed systems, the resolution deteriorates quickly away from the focal plane. This is a particularly difficult problem in microendoscopy as there is often no fine focus control at the distal tip due to size restrictions. To avoid out-of-focus haze, confocal sectioning can be employed, restricting collected signal to a thin section near the MOF facet i.e. the distal face of the MOF (lensless systems) or the focal plane (lensed systems). However, this can make focusing even more difficult since signal is confocally rejected outside of the thin optical section. In many cases, it would be ideal for microendoscopic systems to collect an "all-in-focus" image over an extended depth of field, where objects appear sharp even if they are not precisely located at the focal plane or MOF facet.

In other types of imaging system, the depth of field can be extended by restricting the collection aperture to increasingly paraxial rays. This reduces the size of the blur circle for out-of-focus objects, thereby sharpening the image over a range of depths. However, MOFs are not equipped with an adjustable aperture, which precludes this mechanism for depth of field control.

Previous attempts at increasing depth of field in endoscopy have relied on mechanical engineering at the distal tip, resulting in larger, more complicated probes.

Other techniques for imaging through single core multimode fibers with an extended depth of field require the use of coherent light. As a result these techniques are highly sensitive to fiber bending, making their application to real-world situations difficult. Moreover techniques for extended depth of field imaging through multicore fibers using coherent light that are insensitive to fiber bending require sophisticated image reconstruction algorithms that tend to fail for complex objects.

Accordingly it is an object of the present invention to provide a method of generating images from light received via a MOF that addresses at least in part one or more of the drawbacks discussed.

Reference to any prior art in the specification is not an acknowledgment or suggestion that this prior art forms part of the common general knowledge in any jurisdiction or that this prior art could be combined with other pieces of prior art by a skilled person in the art.

SUMMARY OF THE INVENTION

In a first aspect the present disclosure provides a method for generating an image from light received by an imager via a multiplicity of waveguides, the method including:

receiving a digital image containing a plurality of pixels; the digital image including a plurality of regions within it wherein each of said regions corresponds to a waveguide core and includes a plurality of pixels, said digital image also including pixels that correspond to interstitial space between said waveguide cores;

defining a first subset of pixels within each region which at least partly correlates with light having been received at a corresponding core in a first spatial arrangement, wherein said subset includes less than all of the pixels within a region; and generating a first image from the first subset of pixels from said regions.

Generating the first image preferably includes:

for each region, determining the average pixel value for said pixels in the first subset and allocating said average pixel value as the pixel value for at least one pixel within said first subset of pixels. The method preferably includes generating pixel values for pixels not being said at least one pixel.

In an embodiment, the average pixel value is allocated to one pixel within said first subset of pixels. Most preferably the average pixel value is allocated to a pixel lying on a predefined position representing a center of the waveguide core in the image. That average pixel value may also be allocated to all pixels in a group of pixels at or around said predefined position representing said waveguide core center.

Generating the first image can include:

generating pixel values for pixels not being said at least one pixel (e.g. a center pixel or centrally located group of pixels). Preferably generating pixel values for pixels not being said at least one pixel includes any one of the following:

allocating pixel values according to a pixel value distribution function centered on said at least one pixel; or allocating pixel values by interpolating between said at least one pixel of neighbouring regions.

Hence in one variant the method involves determining an average pixel value for the pixels in said first subset of pixels within a region, allocating that average value to a nominated pixel (or nominated group of pixels) at a position representing the waveguide core center of that region, and assigning values to the remaining pixels by interpolating (eg. by way of linear interpolation) between the nominated pixels (or respective nominated groups of pixels) of mutually neighbouring regions.

The first subset of pixels can include all pixels within a predefined radius from the center of the region. That radius may be substantially smaller than the radius of the waveguide core. Alternatively, the subset could be any other shaped or located region as desired.

The method may further include:

generating a second image from said received digital image, and combining the second image with the first image to generate a final image.

The second image may be generated in a similar manner to the first image. In this regard this can be performed by:

defining a second subset of pixels within each region, wherein said subset includes less than all of the pixels within a region, and is different to the first subset of pixels; and generating the second image from the second subset of pixels from said regions.

In an embodiment, one of the first and second subsets may comprise a subset of all of the pixels within the region except for pixels partially or wholly corresponding to the interstitial space between the waveguide cores (ie. fiber cladding and void space). In that case, the other of the first and second subsets represents a smaller area of the region, preferably a substantially smaller area.

Generating the second image can include:

for each region, determining the average pixel value for said pixels in the second subset and allocating said average pixel value as the pixel value for at least one pixel of said second subset of pixels. Generating the second image can include:

generating pixel values for pixels not being with the at least one pixel within the second subset of pixels.

Generating pixel values for pixels not being said at least one pixel within the second subset of pixels may further include any one of the following:

allocating pixel values according to a pixel value distribution function centered at said least one pixel within each region; or allocating pixel values by interpolating between the pixel values in the second subset of neighbouring regions.

Hence in one variant the method involves determining an average pixel value for the pixels in said second subset of pixels within a region, allocating that average value to a nominated pixel (or nominated group of pixels) at a position representing the waveguide core center of that region, and assigning values to the remaining pixels by interpolating (eg. by way of linear interpolation) between the nominated pixels (or respective nominated groups of pixels) of mutually neighbouring regions.

The second subset of pixels includes all pixels within a second predefined radius from the center of the region. That radius may be substantially smaller than the radius of the waveguide core. As with the first subset of pixels, the second subset of pixels can include any shaped subset of pixels.

Combining the second image with the first image may involve, for each region, using one of the first and second images to modulate, weight or otherwise modify the other of the first and second images. The modified images for all regions are then combined to generate a modified digital image across the multiplicity of waveguides.

Combining the second image with the first image includes optionally scaling the brightness of one or both images and subtracting the second image from the first image. The brightness scaling is preferably carried out so that the total intensity of both images is equal. It will be understood that other suitable approaches to combining the second image with the first image may be used.

By appropriate selection of regions, this approach has the effect of constricting the numerical aperture of each waveguide, by selectively removing light near the periphery of each core and calculating difference in the light levels in that (first) image with those of the unfiltered (second) image.

The first image preferably has a larger effective depth of field than the second image.

Preferably the generation of the first image is biased towards the selection of light rays received at the waveguide within a first angular range; and the generation of the second image is biased towards the selection of light rays received at the waveguide within a second angular range.

Preferably the second angular range is wider than the first angular range.

In some embodiments of any of the methods defined above the method can further include:

defining at least one further subset of pixels within each region which at least partly correlates with light having been received at a corresponding core in a corresponding further spatial arrangement, wherein said further subset(s) includes less than all of the pixels within a region;

generating at least one corresponding further image from said received digital image; and combining according to weightings the first image and said at least one further image to generate a final image. The at least one further images can include the second image.

The predetermined weighting can be determined by a calibration process.

In another aspect there is further disclosed herein a method for improving the apparent depth of field of an image captured via a multicore optical fiber (MOF), the digital image containing a plurality of pixels and the digital image including a plurality of regions within it wherein each of said regions corresponds to a core of the MOF and includes a plurality of pixels, said digital image also including pixels that correspond to interstitial space between said waveguide cores, said method including generating a first image with an improved depth of field by:

defining a first subset of pixels within each region which at least partly correlates with light having been received at a corresponding core in a first spatial arrangement, wherein said subset includes less than all of the pixels within a region;

for each region, determining the average pixel value for said pixels in the first subset and allocating said average pixel value as the pixel value for at least one pixel of said first subset of pixels; and generating pixel values for pixels not being said at least one pixel.

Generating pixel values for pixels not being said at least one pixel within the first subset of pixels can include any one of the following:

allocating pixel values according to a pixel value distribution function centered on said at least one pixel in each first region; or allocating pixel values by interpolating between the pixel values in the first subset of neighbouring regions.

The method may further include:

generating a second image from said received digital image, and combining the second image with the first image to generate a final image with improved depth of field;

wherein the second image is generated by:

defining a second subset of pixels within each region, wherein said subset includes less than all of the pixels within a region, and is different to the first subset of pixels; and generating the second image from the second subset of pixels from said regions.

In preferred embodiments the first image has a larger effective depth of field than the second image.

The generation of the first image is preferably biased towards the selection of light rays received at the waveguide within a first angular range; and the generation of the second image is biased towards the selection of light rays received at the waveguide within a second angular range.

The second angular range is preferably wider than the first angular range.

Systems configured to perform these methods (e.g. imaging systems, and image processing systems) also constitute further aspects of the present disclosure.

Further aspects of the present disclosure relate to light field imaging.

In particular, in a further aspect the present disclosure provides a method of determining a light field approximation corresponding to a pair of images generated from light received by an imager via a multiplicity of waveguides, said light field approximation to be used in image processing, the method including:

obtaining a pair of images, the first member image of the pair having a first depth of field and the second member image of the pair having a second depth of field; wherein said first member image and second member image have the same focus position;

generating a difference image from the pair of images;

calculating a light field approximation from said difference image.

The process of generating a difference image may first involve intensity scaling of at least one of the images. This intensity scaling preferably involves dividing each pixel value by an average pixel value for that image, so that the total intensity of the pair of images is equal.

The process of calculating the light field approximation may include using an assumed angular distribution of light propagation about a mean ray orientation.

The assumed angular distribution may be Gaussian.

The second member image can be obtained using the method of an embodiment of any one of the above aspects of the disclosure.

The first member image can be obtained using an embodiment of the first aspect of the present disclosure and the first member image and second member image use different first subsets of pixels within each region.

Preferably, the first member image is obtained from the same digital image as the second member image, and is generated from substantially all pixels within the regions of the digital image corresponding to the waveguide cores.

In a further aspect there is disclosed a method of generating an image comprising:

obtaining a pair of images, the first member image of the pair having a first depth of field and the second member image of the pair having a second depth of field; wherein said first member image and second member image have the same focus position;

determining a light field approximation using a method embodying the previous aspect of the disclosure;

processing an image according to the light field approximation to generate a final image.

Processing the image according to the light field approximation can include any one or more of the following:

reconstructing an image having a different focus position;

reconstructing an image having a different viewpoint than the received images;

reconstructing a 3D perspective of the image.

Processing of the image in this or any of the other aspects of the invention disclosed herein may involve assuming a non-linear stereo disparity of a light source with increasing distance from the light source.

In a further aspect, there is provided method for generating one or more images from light received by an imager via a multiplicity of waveguides, the light generated from a light field incident on said multiplicity of waveguides, the method including:

receiving a digital image containing a plurality of pixels, the digital image including a plurality of regions, each of said regions corresponding to a waveguide core and including a plurality of pixels;

processing the image intensity pattern across each of said regions to determine a light field angular dimension measure for that region;

applying the angular dimension measure to one or more of the pixels included in each region and to produce one or more sets of modified image data;

using the one or more sets of modified image data to generate one or more images.

The step of processing the image intensity pattern across each of said regions may include the step of analysing each region by way of a simulated aperture technique involving, for each region, a computational comparison of image intensity under a first computational aperture with image intensity under a second computational aperture. The pixels in one of said first and second computational apertures may comprise a subset of the pixels in the other of said first and second computational apertures, or the set of pixels in each computational aperture may be different, depending on the particular light field angular dimension measure to be extracted from the processing step.

Alternatively or in addition, the processing of the image intensity pattern across each of said regions may involve a pattern matching algorithm comparing the image intensity pattern with stored patterns. The stored patterns may be generated for each of said multiplicity of waveguides by way of a pattern calibration process.

As noted above, in a further aspect, the present disclosure also provides an imaging system. The imaging system can comprise:

a multicore optical fiber (MOF) extending from a proximal end to a distal end;

a light source for illuminating a scene at the distal end of the MOF;

an imager arranged with respect to the proximal end of the MOF to capture an image of light propagated along the MOF;

a data processing system configured to receive images captured by the imager and configured to execute instructions that cause the data processing system to perform a method embodying any of the aspects disclosed herein.

Preferably the MOF comprises an endoscope.

The present disclosure describes the use of various illumination geometries for the object or scene to be imaged. In one or more embodiments, the described methods and systems utilise reflection, transmission, fluorescence or combinations thereof.

As noted above, in a further aspect, the present disclosure also provides an image processing system comprising at least one processing unit and at least one memory for storing instructions for execution by the at least one processing unit, the instruction being executed to perform a method embodying any of the aspects disclosed herein.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

BRIEF DESCRIPTION OF THE DRAWINGS

FIG. 9a shows cloth fibers imaged using the standard full aperture approach (left column), compared to an embodiment of the present invention (right column) using both 10× and 20× objective lenses. FIG. 9b shows the intensity profile along the lines shown in the middle row of FIG. 9a.

DETAILED DESCRIPTION OF THE EMBODIMENTS

Figure 1:
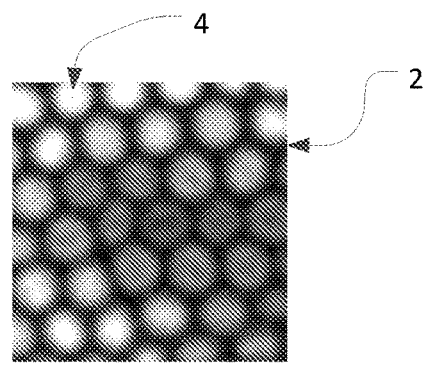
FIG. 1 represents a portion of a raw image obtained from a MOF by the imager, showing the MOF cores and interstitial areas.
Figure 2:
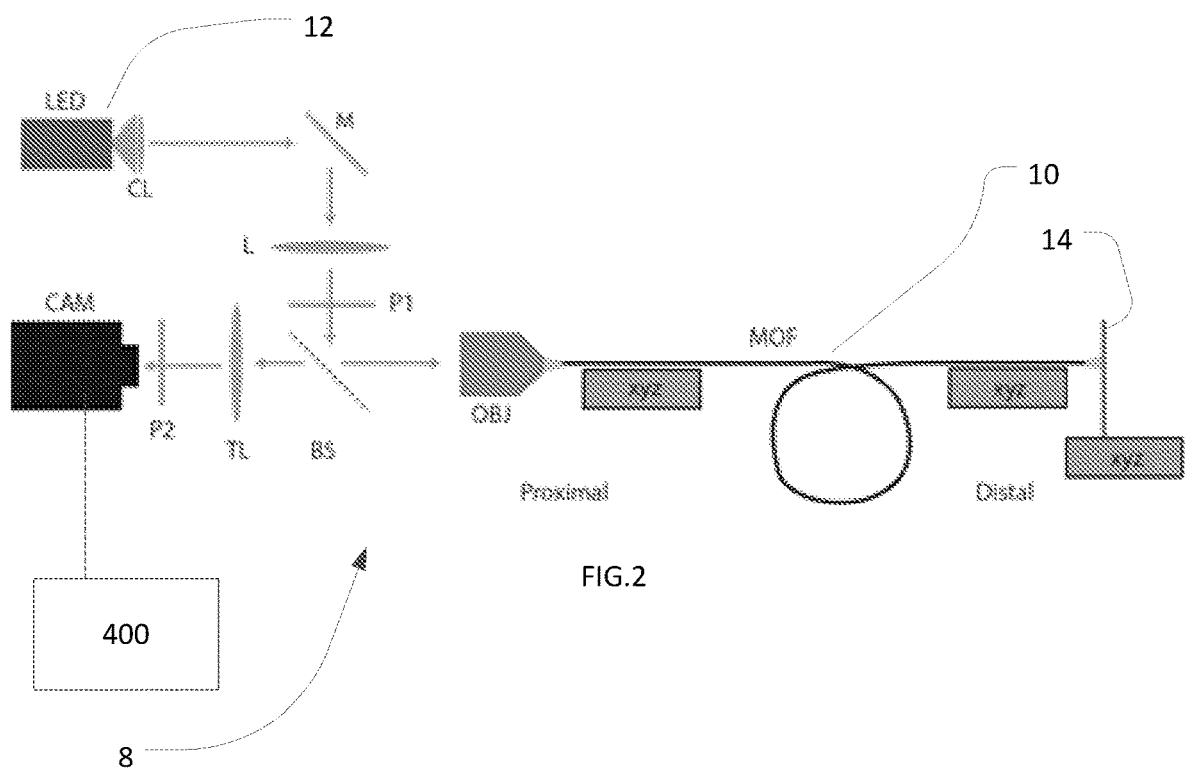
FIG. 2 is a schematic MOF imaging system, used in capturing images that are can be processed according to an embodiment of the present invention.

FIG. 2 illustrates a schematic of an exemplary optical set up of a MOF in an imaging system 8 arranged to image a prepared sample to illustrate embodiments of the present invention. The imaging system can be an endoscopy system. Preferably it is coupled to, or includes, a data processing system 400 for processing image data from the imaging system 8.

The proximal facet of an MOF 10 (e.g. a (Fujikura FIGH-30-600S or FIGH-10-350S) is illuminated with incoherent light from a LED 12 (e.g. Thorlabs M565L3 LED, 565 nm center wavelength). Total illumination intensity at the distal end of the MOF is ~10 µW in this example. Light from the LED 12 is collimated with a collimating lens (CL) via a mirror (M), a 200 mm lens (L), a polarizer (P1), a beam splitter (BS) and a 20× objective lens (OBJ). The illumination source 12 is linearly polarized in order to facilitate rejection of light reflected off of the proximal facet of the MOF. Both ends of the MOF 10 and the sample 14 are affixed to independent 3-axis translation stages (xyz). There is preferably no lens between the distal MOF facet and the sample, although some embodiments of the present invention may use such a lens arrangement.

Light reaching the distal end of the MOF illuminates the sample 14, after which reflected light couples back into the MOF 10. The back-reflected light couples into a variety of modes depending on its angle of incidence at the distal fiber facet. The output intensity pattern within multiple cores at the proximal end is imaged via a microscope objective (e.g. Olympus Plan Achromat 20× 0.4 NA), the beam splitter (BS), a 200 mm tube lens (TL) and a second polarizer (P2). The polarization axes of P1 and P2 are orthogonal to filter out reflected light at the proximal facet. The image is captured by a camera (CAM) (e.g. monochrome, camera with a 10 ms integration time, Thorlabs DCC3240M). In this example, the core and cladding refractive indices of the MOF are ncore=1.5 and nclad=1.446, respectively, resulting in an NA of 0.398, that roughly matches the 20×, 0.4 NA objective lens (OBJ).

The present inventor has realised that the property—that light arriving at the distal (receiving) end of the multiple core fiber from different directions will be propagated to the proximal end and received at the imager with different spatial intensity patterns—can be used to emphasise or de-emphasise light received from certain directions in a processed image. The invention therefore arises from the realisation that the MOF transmits 3D information in the form of light field information (the spatio-angular distribution of light rays incident on the distal end of the MOF), and the angular dimension of the light field is modulated into the intra-core intensity patterns of the fiber bundle, these patterns having been hitherto ignored. As discussed further below, these intensity patterns arise due to angle-dependent modal coupling, and the present invention involves relating these patterns to the angular dimension of the light field.

A key observation is that light incident on a fiber core at varying angles will produce varying intensity distributions at the output of the fiber core. Specifically, light rays that hit the fiber core straight-on (paraxial rays) tend to mostly excite the fundamental mode of the fiber, resulting in an output pattern where most of the light is concentrated in the middle of the core. On the other hand, as the angle of incidence is increased, the output light density light at the output of the fiber core tends to move towards the periphery of the core. Moreover, the inventor has realised that by emphasizing light arriving approximately parallel with the axis of the distal end of the fiber, an image with increased depth of field can be generated.

In accordance with the invention, these intensity patterns, arising due to angle-dependent modal coupling, are quantitatively related to the angular structure of the light field.

Embodiments of the present invention create an image using a "simulated aperture" applied to each core of the optical fiber. The simulated aperture is applied by weighting the image generation process to selectively emphasise a subset of pixels from the image that corresponds to one or more spatial regions of each core. In one form the simulated aperture is applied by selecting a subset of pixels containing only pixels within a given radius of the center of each core. In some embodiments the subset of pixels corresponding to each core may not be centered on the center of each core. For the avoidance of doubt the subset of pixels constituting the "simulated aperture" need not be a single spatially contiguous subset, but may be comprised of sub-subsets. Moreover the subset of pixels may form any appropriate shape.

Embodiments can be applied to multicore optical fibers used in either contact mode (lensless) or lensed mode.

Figure 3:
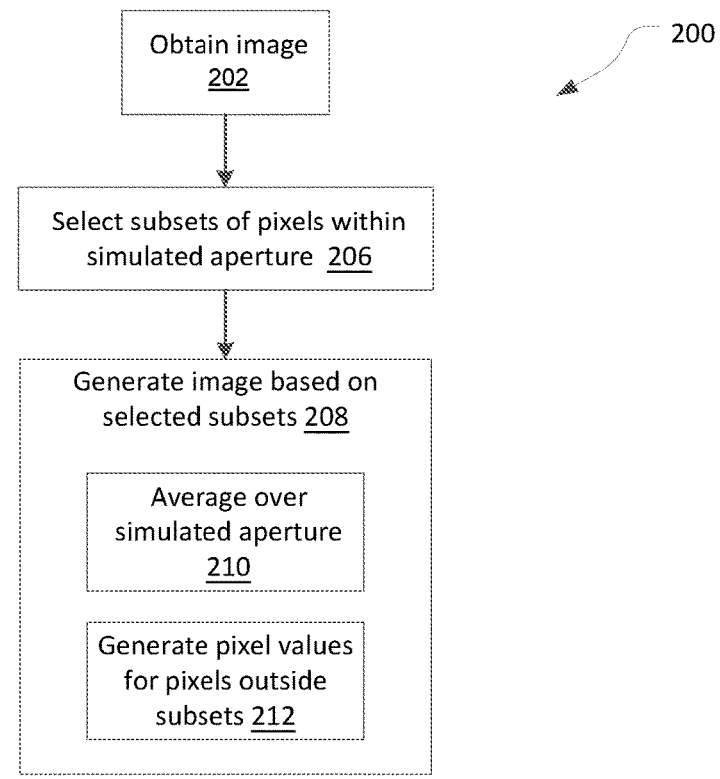
FIG. 3 is a flowchart of a first image processing method according to an embodiment of the present invention.

FIG. 3 illustrates an exemplary method of the present invention that can be used to generate an image with a larger DOF than the originally captured image 202, it removes contributions from rays arriving at highly oblique angles by applying a simulated aperture to the received image. As stated above, paraxial rays mostly contribute to the intensity in the middle of the fiber core, whereas oblique rays tend to produce patterns where the intensity is pushed towards the periphery of the core. Thus by reconstructing an image by using only the central pixels at from each core it is possible to somewhat reject oblique rays, or at least skew image generation towards the inclusion of a greater proportion of paraxial rays. This has been discovered to have the effect of increasing the DOF compared to using all pixels from each core or downsampling the raw fiber facet image.

The method 200 begins by receiving an original image from a MOF e.g. using a setup such as that illustrated in FIG. 2. Next, in step 206, a subset of pixels from the regions in the image which correspond to waveguide cores (i.e. the portions of the image that relate to the interstitial spaces are ignored) are selected and used to generate an image in step 208. The regions can be conceptually thought of as simulated apertures that are applied computationally, which have the effect of being more or less selective to light received at different arrival angles at the distal end of the MOF.

In some embodiments this may be a precondition of the selection of the subsets of pixels to identify the regions in the image corresponding to the waveguide cores. This can be performed using automated image analysis techniques or alternatively it can be determined that the waveguide cores are spatially located in a known pattern, e.g. a regular grid, and hence the locations of the regions in the image are known. In some embodiments identification of the regions in the image comprising cores could be determined by a process of taking a reference image with a mirror in place of a sample. This image would have high contrast between core and cladding in the image and can be used identify core locations more easily.

As will be appreciated by those skilled in the art, in embodiments of the present invention, other image processing techniques may also be employed to improve image quality. For example, a background image can be acquired with no sample present and then subtracted from each raw camera image before further processing.

Next in step 208 the image is generated based on the pixels within the simulated aperture. This can involve averaging the pixel value over the simulated aperture 210 and allocating this value to the pixel lying at the core's center. Next the method includes generating pixel values between the core centers (step 212). Step 212 may include allocating pixel values by applying a pixel value distribution function centered on each core center; or interpolating between the pixel values of neighbouring core centers.

In a preferred form, after averaging the intensity within each simulated aperture, each region's average value is allocated to a grid position in the image, representing that core's center and the image is resampled. In the resampled image, values corresponding to each region (i.e. core) position on the grid corresponds to its position on the fiber facet. The image is resampled using a Gaussian intensity profile with a full width at half maximum (FWHM) equal to twice the grid spacing. The Gaussian's FWHM can be adjusted to provide a balance between signal-to-noise ratio and resolution. The inventor has found that although a FWHM of twice the grid sampling low pass filters the image slightly, it improves image resolution by averaging high spatial frequency noise from non-uniform core spacing. The peak value of the Gaussian representing a given core is made equal to the mean intensity within the selected subset of pixels within the core region (i.e. simulated aperture).

Figure 4:
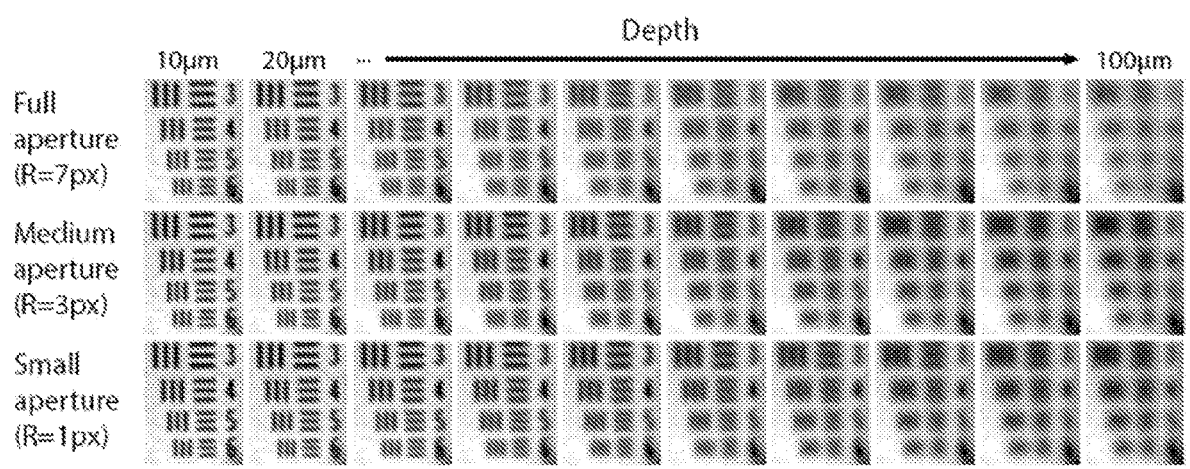
FIG. 4 illustrates a series of images to illustrate an output from two embodiments of the present invention compared to an original image series. In this example the images show a portion of group 5 of a USAF 1951 target.

FIG. 4 illustrates a series of images to illustrate an output from two embodiments of the present invention compared to an original image series. In this example the example images show a portion of group 5 of a USAF 1951 target. Each column of images displays a corresponding image acquired at a given depth. Different columns represent different depths and step from left to right in 10 μm increments from 10-100 μm.

The top row shows the original image series. As will be appreciated the original image series has been processed to filter out pixels of the interstitial spaces between fiber cores. This is performed using a method similar to that described above. The original image series is constructed by integrating all of the signal within each core (by assuming a core radius of R=7 pixels) followed by resampling the cores onto a grid. These are referred to as "full aperture" images.

The images in the second and third rows of FIG. 4 are constructed using a simulated aperture smaller than the whole width of the fiber. The second row uses a "Medium" aperture and averages the intensity of pixels within R=3 of the core center. The bottom row uses a "small" aperture and averages the intensity of pixels within R=1 pixels of the core center.

As can be seen, the reduced size simulated aperture increases contrast at larger depths. For example, the 3rd element grating (top of each image) is resolvable at 70 μm with a small simulated aperture but unresolvable using the full aperture. None of the gratings imaged can be resolved in a full aperture image beyond a depth of 60 μm. In practice, higher order modes will contribute a small amount of light to the central pixels and diffraction imposed by the microscope objective will also tend to mix light from the edge and center of the cores in the camera image. As a result, the increase in contrast between full and small aperture images is modest in these examples.

Figure 5A:
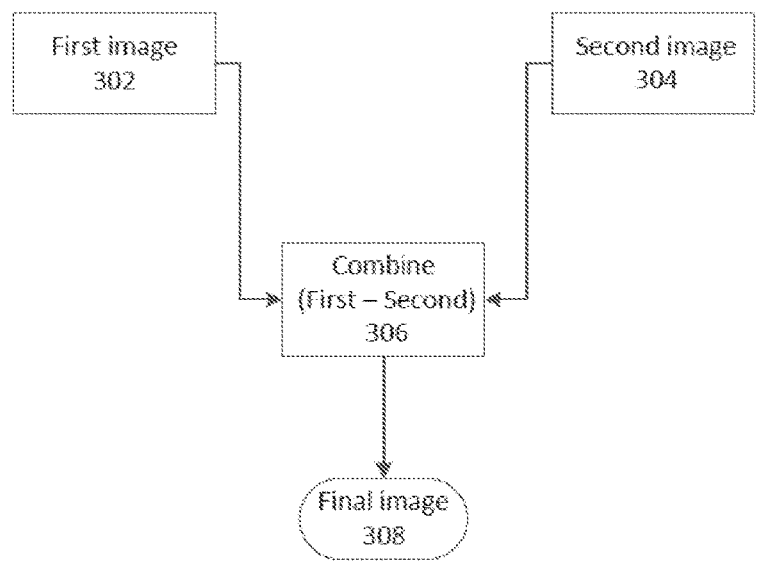
FIG. 5A is a flowchart of a second image processing method according to an embodiment of the present invention.

FIG. 5A illustrates a further embodiment of the present invention which may further improve DOF of the generated image. In FIG. 5A a first image 302 is generated using the method of FIG. 3, using a first simulated aperture. A second image 304 can also be obtained, e.g. either the original image or generated using the method of FIG. 3, using a second simulated aperture that is different to that used to generate the first image 302. The first image 302 is combined with the second image 304 to generate a final image 308. The combination step at 306 is a simple deblurring step and further increases the image quality. In this step an image created using all the pixels within the fiber core (or a simulated aperture that effectively provides a blurry, short DOF image compared to that of the first image 302) is subtracted from the first image 302 that was created using only the central pixels. In doing so, the out of focus light is subtracted from the first image 302.

Figure 6:
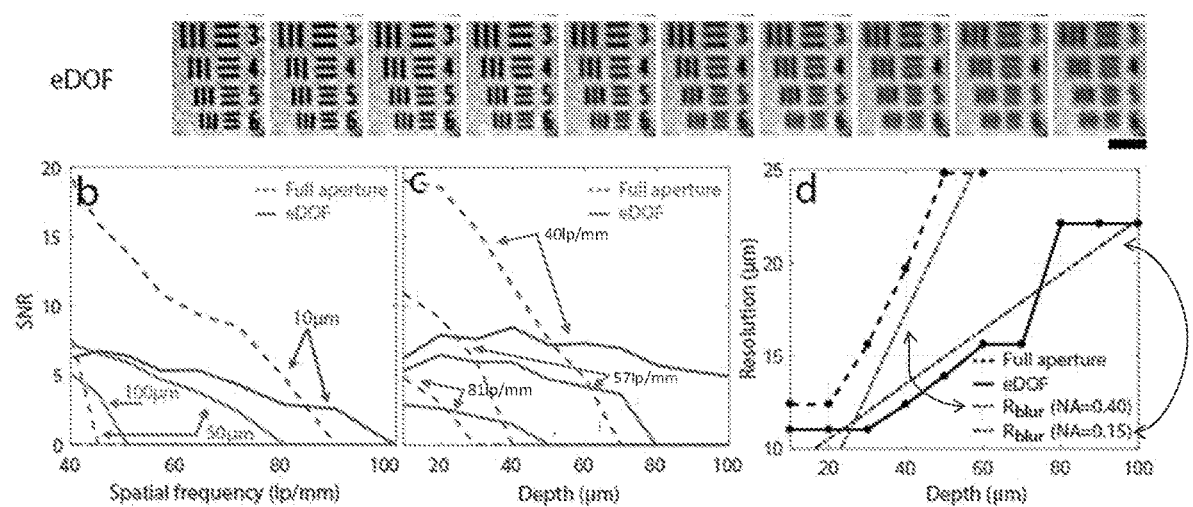
FIG. 6 illustrates an image series (labelled eDOF for "extended depth of field" image) generated using an embodiment of the process of FIG. 5A. A series of plots comparing the image series of FIG. 6 to that of FIG. 4 are also shown.

FIG. 6 illustrates an image series (labelled eDOF for "extended depth of field" image) generated using an embodiment of the process of FIG. 5A. More specifically they were obtained by subtracting the R=3 pixel radius image series from the R=1 pixel radius image series of FIG. 4 (Scalebar: 100 μm).

Returning briefly to the basic principle behind the invention, consider a MOF illuminated by a light ray (or plane wave) travelling towards the input facet, as shown in FIG. 2. The output light intensity profile within each core of the MOF depends on the orientation of the exciting plane wave.

FIG. 7a illustrates a ray impinging on a fiber core at the input facet at an orientation described by the angle of incidence θ and the azimuthal angle φ. These angles relate to the orientation of a light ray and not to the core geometry.

FIG. 7b shows the simulated input core intensity distributions arising from plane waves oriented at angles (θ, φ) (Scalebar: 5 μm) Intensity distributions are calculated by forming an incoherent superposition of the fiber's linearly polarized (LP) modes. The amplitude of each LP mode in the superposition is given by the coupling efficiency of a plane wave oriented at angles (θ, φ). The intensity distributions are then integrated over the emission spectrum of the light emitting diode (LED) used in the experiments (Thorlabs M565L3 LED, 565 nm center wavelength, FWHM ~100 nm). The central image is the intensity pattern at the input, resulting from a normally incident plane wave—i.e. paraxial rays. The corner images are the intensity patterns near $\theta c=\sin-1$ (NAc).

The intensity patterns are assumed to be unchanged from input to output facet, due to the temporally incoherent nature of the illumination. That is, the intensity distributions simulated in FIG. 7b are located at the input facet. Since the field within the core is temporally incoherent, it is expected the output intensity pattern to be largely unchanged from the input. This has been verified experimentally by imaging the output of a fiber core subjected to plane wave excitation input at various angles. FIG. 7d illustrates an experimentally recorded output intensity from a single core at the output facet for varying plane wave input angles (θ, φ) using the setup of FIG. 2 (Scalebar: 5 μm). A plane wave input was achieved by digitally raster-scanning a small circular aperture over a digital micromirror device (DMD) placed conjugate to the back pupil plane of the microscope objective. The measured output intensity distributions in FIG. 7d distributions show good qualitative agreement with those produced by the simulation for the input facet (FIG. 7b), supporting the view that the intensity profile is relatively unchanged from input to output facets. Given this observation, the intensity pattern at the core output can be used as a proxy for angular filtering of light rays at the core input.

The relationship between the input plane waves and the output intensity pattern within a core can be expressed via the matrix equation Ax=b, where the columns of A are the intensity patterns created by particular plane wave input orientations (i.e. the patterns in FIG. 7d, rearranged into vectors), the vector x is the fraction of input intensity at a given plane wave orientation, and the vector b is the recorded core output intensity pattern. That is, the output intensity pattern within a core is a linear combination of the intensity patterns created by individual plane waves (or rays). By solving for x, it is possible to isolate the contribution that coupled into the input facet of the core at a low angle, thereby reducing the collection aperture and increasing the depth of field. However, the coupling matrix A is different for each core in the fiber due to the nonuniform geometry.

Therefore, in order to solve for the contribution for each ray orientation within each core (x), one requires a measurement of the angular coupling matrix A for each core, followed by matrix inversion at each core separately. This could be achieved via careful calibration or simulation.

Instead of pursuing calibration, preferred embodiments of the invention use an approach that does not require calibration. The preferred technique starts from the observation that rays travelling normal to the facet interface (central image in FIG. 7(b), θ=0) tend to excite the fundamental mode with intensity peaked in the core center. Oblique rays (large θ) excite modes with intensity localized further towards the core/cladding interface. Thus, for the fundamental mode (l=0) the maximum excitation efficiency occurs at θ=0. All incident power is coupled into the fundamental mode at normal incidence, but is split among the fundamental and increasingly higher order modes as θ increases. Based on this, it is possible to extract information regarding higher order modes of the received light by weighting the image towards the interface between the core and the edge of the fiber (the core/cladding interface).

Figure 7:
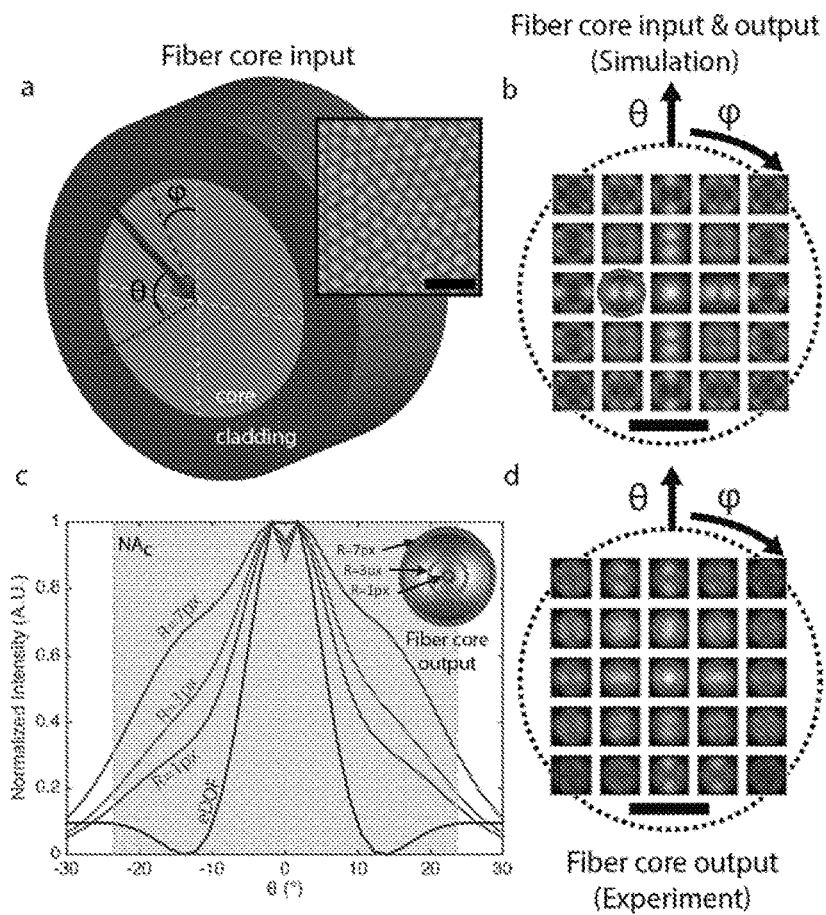
FIG. 7a illustrates a ray impinging on a fiber core at the input facet at an orientation described by the angle of incidence 6 and the azimuthal angle φ.
FIG. 7b shows the simulated input core intensity distributions arising from plane waves oriented at angles (θ, φ) (Scalebar: 5 µm). Specifically FIG. 7c plots the simulated normalized intensity within a full aperture image (R=7 px) and two simulated apertures with R=3 px and 1 px for the fiber core input that is circled in FIG. 7b.
FIG. 7d illustrates experimentally recorded output intensity from a single core at the output facet for varying plane wave input angles (θ, φ) using the setup of FIG. 2.
FIG. 7E illustrates simulated angular PSFs that have been normalized to the aperture area.

In preferred embodiments the invention is concerned with coupling efficiency as a function of input angle, and how this varies for different subregions at the core output. FIG. 7c plots the normalised total intensity within different subregions of the simulated input/output core image (FIG. 7b) as a function of incident angle θ. The inset in FIG. 7c indicates each simulated aperture size relative to the full core size, superimposed over the intensity pattern circled in FIG. 7b. In FIG. 7, 1 px=238.5 nm and matches the experiments in FIGS. 4 and 6. The shaded background indicates the range of acceptance angles within the NA of the MOF.

Figure 7E:
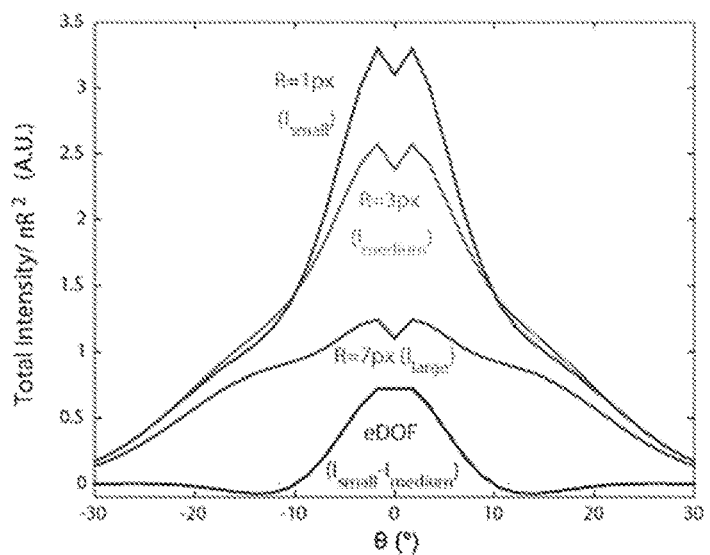

Specifically FIG. 7c plots the simulated normalized intensity within a full aperture image (R=7 px) and two simulated apertures with R=3 px and R=1 px for the fiber core input that is circled in FIG. 7b. The curve labelled "eDOF" is the difference between aperture area-normalized R=1 px and R=3 px curves. All curves in FIG. 7c are normalized to have a maximum value of 1. Area normalization is performed as illustrated in FIG. 7E. FIG. 7E illustrates simulated angular PSFs that have been normalized to the aperture area. Here, the total intensity within each selected subset of pixels imaging the core is divided by the area ($\pi R^2$) or the simulated aperture. The small aperture angular PSF (R=1 px) has the largest magnitude because the mean pixel value is greatest for this subregion. In contrast, the full aperture angular PSF (R=7 px) has the lowest mean value as it contains many dim pixels that lower the mean value. The eDOF curve is calculated as Ismall−Imedium directly using the curves in this plot. This aids to remove remaining oblique rays from the R=1 px image. An offset is added so that the curve is positive everywhere. This curve is labelled "eDOF" in FIG. 7E.

In FIGS. 7c and 7E, the intensity within a small "simulated aperture" of radius R=1 pixel from the core center (1 pixel=238.5 nm), has a sharper angular distribution than "medium" R=3 and "full aperture" R=7 image. This can be seen qualitatively in the example of FIG. 4. As seen in the eDOF plots in FIGS. 7c and 7e the angular PSF can be further narrowed by subtracting the R=3 px curve from the R=1 px curve after normalizing the total intensity of each curve by their respective aperture areas as shown in FIG. 7E.

An image formed by this subtraction process will have an increased resolution compared to the small aperture image at the expense of reduced signal and increased noise (noise from small and medium aperture images are additive). It is also noted that the eDOF PSF has an elevated background level due to the added offset.

Figure 5B:
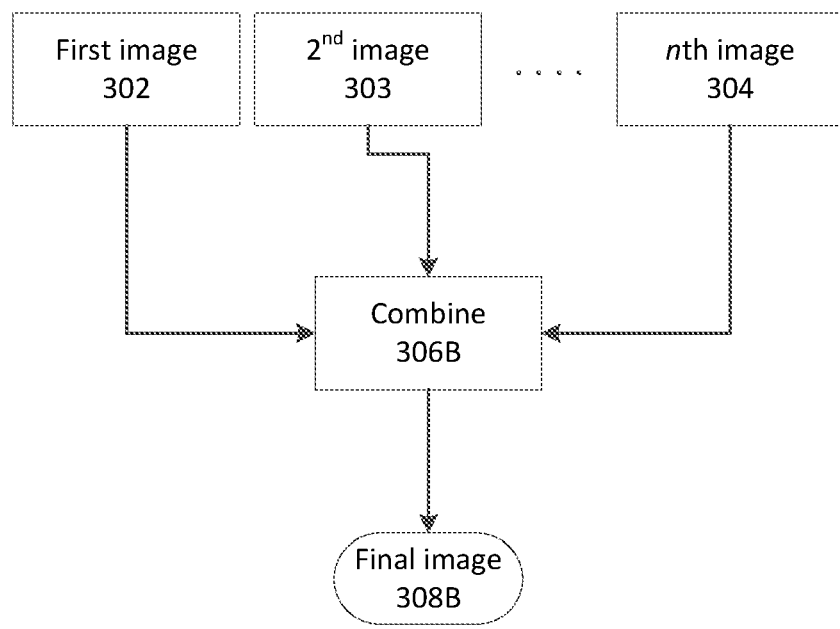
FIG. 5B is a flowchart of a further embodiment of the method of FIG. 5A.

In general, other linear combinations of simulated aperture-filtered images can be used to produce images with varying properties. For example different depths of field, tradeoffs between signal to noise ratio (SNR) and angular PSF width. More generally it is possible to selectively target the imaging of plane waves oriented at any given angles (θ, φ). FIG. 5B illustrates such a process. In this example, n images (302, 303, 304), each of which can be derived from a process similar to FIG. 3, but having different simulated apertures are combined at step 306B. That is each of the n images is generated from a different subsets of pixels from each image core, such that each image correlates with light having been received in a selected spatial arrangement. The images used in such a process, may arise from the average value within any subset of pixels with the core, not necessarily concentric with the core center, as in previous examples.

The combination in step 306B can be performed according to given weightings to generate a final image 308B. The weightings used for the combination can be predetermined by a calibration process, or derived in an optimization process. For example the linear combination to be used in a given situation could be arrived at by optimizing the combination of a set of images on any image metric, such as: contrast, signal to noise ratio or the like. This optimization can be done in a greedy fashion. Prior to combination the n images can be normalized as illustrated in FIG. 7e or the appropriate image normalization factor needed to scale the relative amplitude of the images can be built into weightings applied during combination of the images.

As will be seen the specific process of FIG. 5A is a special case of the process of FIG. 5B in which images generated with centrally-located, circular, simulated apertures are combined, and the weighting applied to image with less angular discrimination is −1.

As can be seen in FIG. 6, the resulting eDOF image shows remarkably increased fidelity, with the top two gratings resolvable for the entire 100 μm depth series. However, the additional contrast of the eDOF images comes at the expense of additional noise, which in turn affects resolution.

Figure 8:
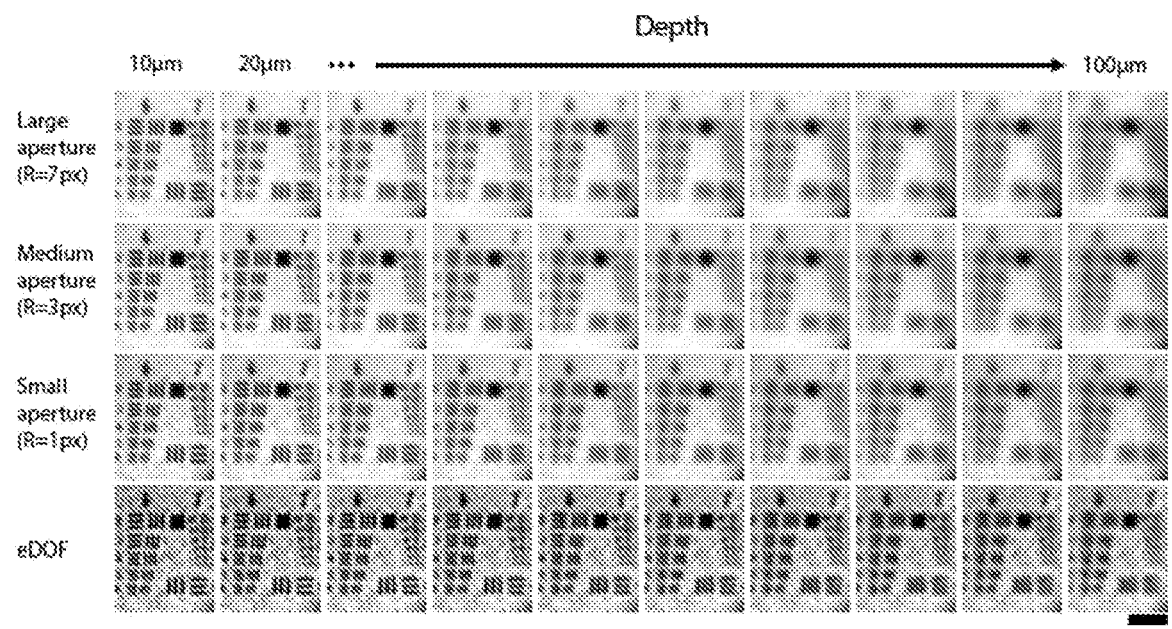
FIG. 8 shows series of images of a portion of groups 6 and 7 of a USAF 1951 target used in experimental testing of an exemplary implementation of the present invention.

FIG. 8 shows series of images of a portion of groups 6 and 7 of a USAF 1951 target. Each column displays the image acquired when the target is placed at a depth of 10-100 μm. The top row shows the original image series, constructed by integrating all of the signal within each core region (R=7 pixels) and resampling onto a grid. The 2nd and 3rd rows are the same as the top row, but integrating only over a subset of pixels having a radius of R=1, and 3 pixels, respectively, centered at each core. The bottom row is the eDOF image, obtained by subtracting the R=3 pixel radius image series from the R=1 pixel radius image series. These images are used in addition to the images in FIGS. 4 and 6 to create the SNR and resolution curves in FIGS. 6*b*, *c*, and *d*. (Scalebar: 100 μm).

In order to quantify the true gain in image quality as a function of depth, the modulation depth of the grating lines for group 5 elements 3-6, and group 6 elements 1-6 are extracted, as shown in FIG. 8, and normalize to the noise in the image. The noise (N) is computed by taking the standard deviation of a group of pixels in a blank region of the image, and the modulation depth (M) is the mean intensity difference between the grating lines and the spaces in between the lines. The MATLAB Findpeaks function is used to locate grating lines, with the requirement that the prominence of each peak must be ≥N/2. If less than three grating lines are resolvable by this criteria, the grating is said to be unresolvable and M is set to zero. This noise-normalized modulation is referred to as the signal-to-noise ratio (SNR=M/N). Conceptually this is similar to the modulation transfer function (MTF) of an imaging system, normalized by the noise equivalent modulation.

Plot 6*b* illustrates SNR as a function of grating spatial frequency at depths 10, 50 and 100 μm for the image series of FIGS. 4 and 6. The SNR=modulation depth of the grating with a given spatial frequency, normalized by the noise in the image. Dotted and dashed curves at the same focal position denote the original full aperture images and the final images (in the corresponding eDOF series of FIG. 6), respectively. At a depth of 10 μm, the SNR of the full aperture image exceeds that of the eDOF image up until 81 lp/mm before becoming unresolvable. Despite lower SNR at low spatial frequencies, the eDOF image has superior resolving power at 91 lp/rm. For larger depths, the eDOF processing becomes highly advantageous across all spatial frequencies. At 50 μm and 100 μm, the SNR of the eDOF images matches or exceeds that of full aperture images for all spatial frequencies. At 50 μm only the 40 lp/mm is resolvable using the full aperture, whereas all gratings up to and including 72 lp/mm are resolvable in the eDOF image. At 100 μm, none of the gratings can be resolved using the full aperture, but in the eDOF images, both the 40 and 45 lp/mm gratings are resolved.

These data can also be plotted as a function of depth for each spatial frequency, as shown in FIG. 6c. In the full aperture images, spatial frequencies of 81 lp/mm become unresolvable before 30 μm, while remaining resolvable beyond 40 μm in the eDOF images. The same trend is found for 57 lp/mm, which is resolvable at depths up to of 30 μm and 70 μm in the full aperture and eDOF images, respectively. For this spatial frequency, the depth of field is increased 2.3-fold. The largest grating period imaged (40 lp/mm) remains resolvable at all depths considered in eDOF images, but only up to 60 μm in the full aperture images. Similarly, the depth of field for the highest frequency grating (81 lp/mm) is improved two-fold from 20 μm in full aperture, compared to 40 μm in eDOF.

The gain in resolution for distant objects is even more apparent when plotting the smallest resolvable grating pitch as a function of object depth as illustrated in FIG. 6d. The slope of this curve indicates the effective aperture size since the radius of the blur circle predicted by geometric optics grows as Rblur=depth×tan θNA. The line corresponding to the expected resolution of the full aperture of the MOF (NA=0.40, dot-dashed line in FIG. 3(d)), has a nearly identical slope to the full aperture dataset (dashed line in FIG. 6d). The best-fit line to the eDOF data (second dot-dashed line in FIG. 3(d)) has a slope corresponding to an NA of 0.15. Thus, for resolution purposes, the eDOF processing employed has effectively stopped down the aperture by a factor of 0.40/0.15=2.67.

Figure 9:
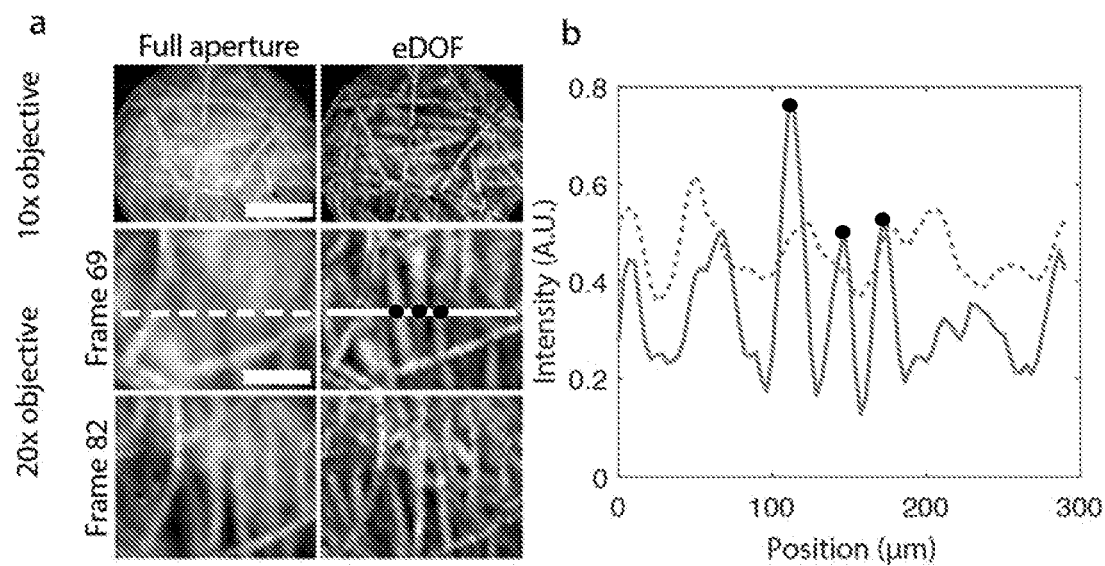

An embodiment of the present invention was then tested with a 3D object, namely cloth fibers from a protective lens pouch. FIG. 9 illustrates "full aperture" and eDOF images of cloth fibers as seen through a MOF. In traditional "full aperture" imaging, only cloth fibers in contact with the MOF facet are imaged with high fidelity. The remaining fibers that are further away from the facet appear blurry and contribute to a diffuse background, decreasing contrast and resolution. FIG. 9a shows cloth fibers imaged using the standard full aperture approach (left column), compared to the present eDOF technique (right column), using both 10× and 20× objective lenses. The 10× objective lens yields a larger field of view than the 20× at the expense of poorer spatial resolution within the cores, and therefore less precise aperture filtering. Nevertheless, the eDOF technique employed still yields markedly improved contrast, even with core regions measuring only ~7 pixels in diameter. A movie of cloth fibers moving in the vicinity of the distal MOF facet, as imaged through the MOF with the 20× objective was generated. The bottom two rows show still frames from this Visualization 1, acquired using a 20× objective. (Scalebar: 100 μm.) The central line (frame 69) denotes the position and direction, respectively, of the intensity profile shown in FIG. 9b. FIG. 9b shows the intensity profile along the lines shown in the middle row of FIG. 9a. The solid curve is the intensity profile in the eDOF image and the dotted curve is the intensity profile in the full aperture image. The dots on FIG. 9a indicate the position of three cloth fibers that are unresolvable in the full aperture image.

Many of the cloth fibers that are not in contact with the MOF facet are still within the depth of field of the eDOF images, and are therefore still resolvable. Of note are three fibers in the middle of the line profile that result in three separated peaks in the eDOF curve (also dotted), yet are not visible in the full aperture curve. This demonstrates that this embodiment of the method not only improves contrast, but fundamentally improves the resolution limit at large depths for 3D structures.

By selecting the subset of pixels from an image region containing each fiber core from which to reconstruct images, preferred embodiments preferentially image light that was coupled into the core at chosen angles. By selecting central pixels, embodiments preferentially select more paraxial rays. As with standard imaging devices, this reduction in collection angle comes with a corresponding increase in depth of field and noise level. For higher spatial frequencies at large depths that are completely suppressed in the low noise, full aperture image, the increased resolution of the eDOF image outweighs the additional noise, resulting in a superior image in preferred embodiments. Particularly preferred embodiments may result in a doubling in depth of field for most spatial frequencies, and an increase in SNR for higher spatial frequencies for distant objects. It is noted that embodiments of the present invention are fundamentally different from image sharpening techniques such as unsharp masking, which can only rescale spatial frequencies, but cannot preferentially filter light based on its input angle.

In addition, more sophisticated approaches to combining images with different simulated apertures, such as HiLo processing used in structured illumination could also be employed, in some embodiments to further increase depth of field and contrast even beyond the illustrative embodiments described in detail here.

Embodiments of this aspect of the present invention provide advantages for MOF imaging, in particular for lensless endomicroscopy probes, as it allows for non-contact imaging without a lens or bulky scanning unit at the distal facet. This means that MOF probes may be kept slim in order to reach narrow constrictions within the body. Obviating the need for a lens assembly at the distal tip also reduces endomicroscope production costs. In cases where a distal facet lens is required (for instance, for increased magnification), embodiments of the present invention are also applicable. In lensed MOF microendoscopy systems, depth of field extension can occur on both sides of the focal plane, instead of only in front of the MOF facet. Furthermore, since embodiments of the present technique are fully incoherent, they may be used with widefield fluorescence imaging. The incoherent nature of technique also makes it insensitive to fiber bending, thereby dispensing with the need for transmission matrix correction after each fiber perturbation.

As discussed elsewhere in this specification, images generated using methods described herein may be advantageously employed in aspects of light field or plenoptic imaging. In other words, applications of the invention use the MOF as a light field sensor. While images relayed by MOFs are inherently 2D, the invention affords the realization that slim MOF-based imagers are capable of recording at least some aspects of the 3D structure of a sample. This is critical in real-world clinical environments where samples are complex undulating structures instead of thin, flat tissue slices mounted on a microscope slide.

The present invention demonstrates that MOFs transmit 3D image information by way of the mode structure within each core, and leverages this information to estimate the average orientation of the light rays hitting each core in the MOF. This angular light ray information along with the raw transmitted image describes what is known as the light field. Given the light field of a scene, 3D perspectives can be reconstructed, objects depths calculated, and the scene can be partially refocused after acquisition.

Light field datasets contain the full $(\theta, \varphi)$ parametrization of incident ray orientation, enabling 3D perspective shifting, depth mapping and refocusing. In conventional light field imaging it is generally required to capture both light intensity data as well as directional (angular) data over the entire image. In practice this typically requires multiple images of a scene to be taken at viewing perspectives or focal lengths, e.g. using a microlens array on the imager to simultaneously capture the images. Or alternatively, a light field estimate can be obtained acquiring two images with different focus positions or by measuring phase shift information.

As will be appreciated, the inventor has surprisingly determined that capturing images with different focus positions or additionally measuring phase shift information are not essential to realise at least some of the benefits of light field photography. In one form, then, the present invention provides a method in which a single image can be used to estimate the light field for a scene captured in that image.

Using the simulated aperture described above the inventor has determined that multiple images having a different effective depth of field (but the same focus position) can be created from a single captured image. These images can then be used to estimate the light field for the single captured image. Because only an average direction of ray propagation can be determined within the light field it is necessary to apply an assumption of the angular distribution of ray propagation at each point. Notwithstanding these limitations, it has been found that the resulting estimated light field can be used in a similar manner to other light field images, namely in processes such as:

Generating images at a different focal length;
Generating images from a different viewpoint;
Generating stereoscopic images by combining two images with spatially separated viewpoints;
Measuring distance to an object in the image.

The inventor has further realised that these techniques can also be applied mutatis mutandis to multiple images of a scene that are captured with the same focus position but different depth of field, regardless of how the images are created (i.e. the two images need not be generated using the simulated aperture technique from a single image described herein, but may be separately captured in a more conventional manner using optical systems to achieve different depth of field.) It should be noted that the term "focus position" includes the concept of a "focal length" when applied to an optical system with a lens.

Figure 10:
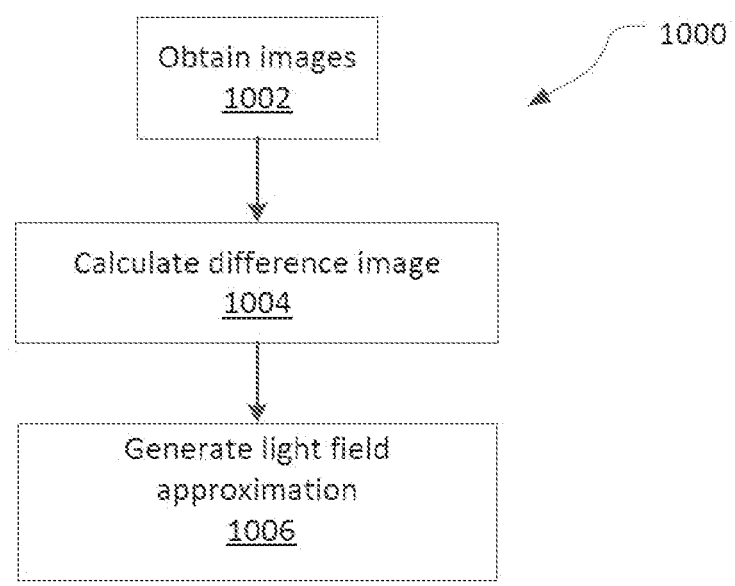
FIG. 10 is a flowchart of a method of estimating a light field for an image using an embodiment of one aspect of the present invention.

FIG. 10 illustrates a method for determining a light field approximation according to an embodiment of the present disclosure.

The method 100 begins at step 1002 by obtaining a pair of images of a scene which each have a different depth of field but the same focus position. In a preferred form the images can be derived using a method according to an aspect of the present invention, e.g. as described in relation to FIG. 3. Next, in step 1004 a difference image is generated from the pair of images. This difference image is used in step 1006 to calculate a light field approximation.

As will be known to those skilled in the art, raw MOF images are often downsampled in order to remove pixilation artifacts imposed by the discrete sampling of the cores. This process assumes that there is no useful information contained within the cores themselves. However, as discussed above in relation to the image generation aspects of the present invention, the cores of an MOF are large enough to support a dozen or so modes in the visible spectrum. Incoherent superpositions of such modes are readily observed at the output facet of an MOF. As the angle of incidence of input light increases, higher order modes are preferentially excited. Consequently, the sub-core output transforms from a central Gaussian spot (fundamental mode) into an expanding ring as the input angle of incidence is increased. In other words, light incident at oblique input angles will tend to result in output light that is localized to the core periphery. Conversely, light incident at small angles remains preferentially at the core center (see FIG. 7d). By generating images using the methods described above the depth of field (DOF) of an image can be enhanced. This does not teach the full orientation of light rays, which is needed for 3D light field imaging. To extract this information, the technique of "light field moment imaging" (LMI) is employed, relating the axial intensity derivative of an image to the average (first moment) ray orientation at each pixel. LMI is described in Orth, A. and Crozier, K. B., 2013. *Light field moment imaging. Optics letters,* 38(15), pp. 2666-2668, the contents of which are incorporated herein for all purposes.

LMI as described therein requires as input a pair of images at slightly different focus positions. However, as noted above, bare MOF imaging probes do not have fine focus control. Instead, embodiments of the present invention use images of different depth of field, e.g. using a simulated aperture as described herein. The inventor has realized that a small simulated aperture size image with a large depth of field is similar to an in-focus image for objects located away from the fiber facet. Similarly, a largely out-of-focus image with a small depth of field created by a large simulated aperture size is intuitively similar to an out-of-focus image for objects located away from the fiber facet. The large simulated aperture image can include a full aperture image. From this point forward, this approximation is referred to as the "aperture-focus approximation". The LMI algorithm can then be used to extract the angular light field moments and construct a light field estimate via the equation:

$$\frac{I_1(x, y) - I_2(x, y)}{\Delta z} = \nabla \cdot I_1(x, y)[M_x(x, y), M_y(x, y)] \quad (1)$$

Where the two images $I_1$ and $I_2$ forming the image pair are small and large simulated aperture images, respectively, and $M_x$ and $M_y$ are the average angle of inclination of rays from z-axis in the x- and y-directions, respectively (the light field moments). Here, $\Delta z$ is not well-defined as two images are being used with different effective apertures instead of different focus locations. As a result, $\Delta z$ is set to an unknown scale factor to be adjusted later. The value of the constant $\Delta z$ has no effect on the resulting visualizations, but simply sets the absolute scale of the resulting parallax.

Figure 11:
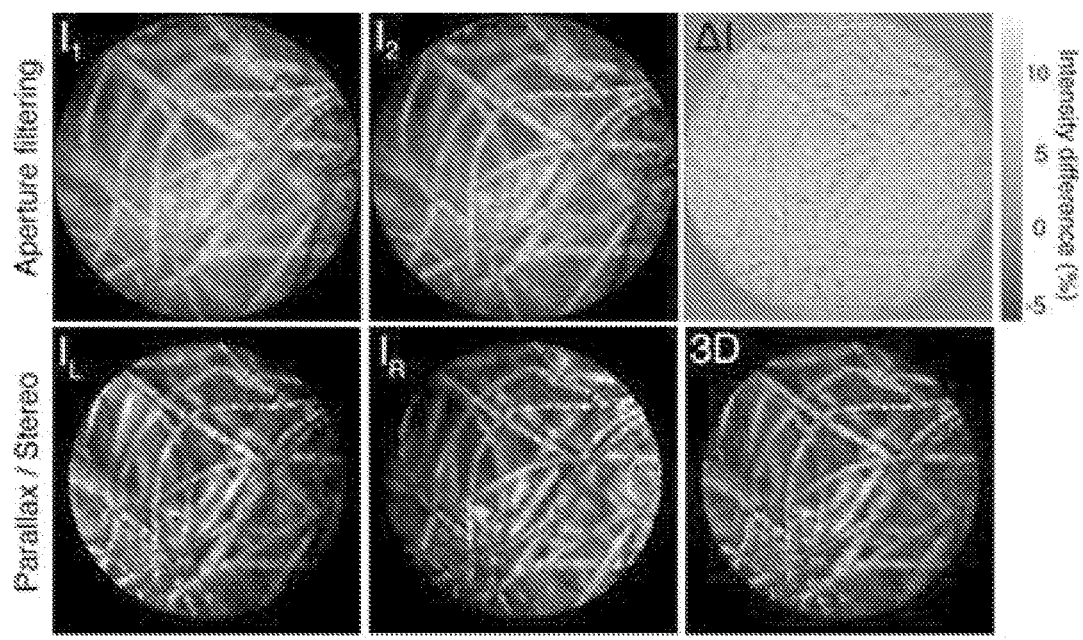
FIG. 11 illustrates first and second images in an image pair used in a method of FIG. 10, and a visualisation of the differences in intensity value between them. The bottom row shows resultant images generated from the light field approximation generated from the images of FIG. 11.

An experimental realization of this approach is shown in FIG. 11. First, images of the target with large and small simulated apertures ($I_1$ and $I_2$, respectively) are obtained. $I_2$ is acquired in the manner set out above. However, for the large aperture image $I_1$ (FIG. 11 top left) the entire core region R (=5 px) is used for image generation in the same way that the Full aperture images of FIG. 4 are created. The small aperture image $I_2$ (FIG. 11 top middle) is generated from a subset of pixels in a small central part of the region (R=1 px).

Because a lensless MOF is used, the entire scene will appear more in focus in $I_2$ than $I_1$ due to the constricted aperture, emulating the defocus process typically associated with LMI. The subtle difference between these two images $\Delta I$ is visualized directly in FIG. 11 (top right).

Using $I_1$ and $I_2$, one can solve for $M_x$ and $M_y$ in Eq. 1 in Fourier space by way of a scalar potential U that is related to the light field moments via ∇U=[$M_x$,$M_y$]. A Gaussian light field estimate L is then constructed using $M_x$ and $M_y$:

$$L(x, y, u, v) = I_1(x, y) \times \exp\left[-\frac{(u - M_x(x, y))^2}{\sigma^2} - \frac{(v - M_y(x, y))^2}{\sigma^2}\right] \quad (2)$$

Where u and v are the angles of inclination from the z-axis in the x- and y-directions, respectively. The parameter a is empirically set to tan θ', and the light field moments are rescaled by a constant factor such that max{$M_x^2$+$M_y^2$}=$\sigma^2$. This ensures that the average light field moment lies inside the collection aperture.

The Gaussian form of L in (u,v) space is an acknowledgement of the fact that if light field is densely sampled in spatial dimension (x,y), it is necessarily low pass filtered in the angular (u,v) dimension due to the diffraction limit. In the most extreme case, this would result in a light field where the angular dimension contains a single broad spot effectively reports on the tilt of rays (or wavefront) at each spatial location, similar to a Shack-Hartmann wavefront sensor.

With the light field L having been estimated according to an embodiment of the present invention, one can perform further image processing as required.

In one example, one may change the virtual viewpoint of a 3D scene by choosing 2D slices (fixed angular (u,v) coordinate) of the 4D light field L. For example, images of the scene as viewed from horizontally opposing viewpoints are: $I_L$=L(x,y,$u_0$,0) and $I_R$=L(x,y,−$u_0$,0), which are shown in FIG. 11 (bottom left, middle bottom). These images form a stereo pair that can then be combined into a red-cyan stereo anaglyph as shown in FIG. 11 (bottom right). This image can be viewed with red-cyan glasses for a 3D effect. Parallax scanning animations can also be constructed viewing the scene from a moving virtual viewpoint. This method is particularly useful in conveying 3D information via motion parallax.

Parallax is a result of depth variation (depth=distance from fiber facet to object) in a 3D scene. Given a light field L, which contains parallax information in all angular directions, one may calculate a depth map. The can be performed using a method set out in Adelson, E. H. and Wang, J. Y., 1992. Single lens stereo with a plenoptic camera. *IEEE transactions on pattern analysis and machine intelligence*, 14(2), pp. 99-106:

$$d = \frac{\sum_P (L_x L_u + L_y L_v)}{\sum_P (L_x^2 + L_y^2)} \quad (3)$$

Where d is the fiber facet to object distance at position (x,y).

In the following, d is referred to as the "depth metric" due to the aforementioned aperture-focus approximation. $L_x$ and $L_y$ are the (discrete) partial derivatives of L in the x- and y-directions, respectively (similarly for $L_u$ and $L_v$ in the u and v directions). The summation proceeds over an image patch P, centered at (x,y) and running over all (u,v) coordinates. The size of the image patch can be adjusted according to the desired smoothness of the result. Typical sizes are 9×9 pixels or larger. The resulting depth maps for a series of images of the USAF target (group 5), illuminated in transmission with white light, are shown in FIG. 12*a*. FIG. 12*b* is a plot of the depth metric as a function of the known ground truth depth (MOF fiber facet to USAF target distance) to the target. The depth metric values are averages over all of all pixels for each ground truth depth. The error bars indicate one standard deviation of the measured depth metric for each ground truth depth.

Figure 12:
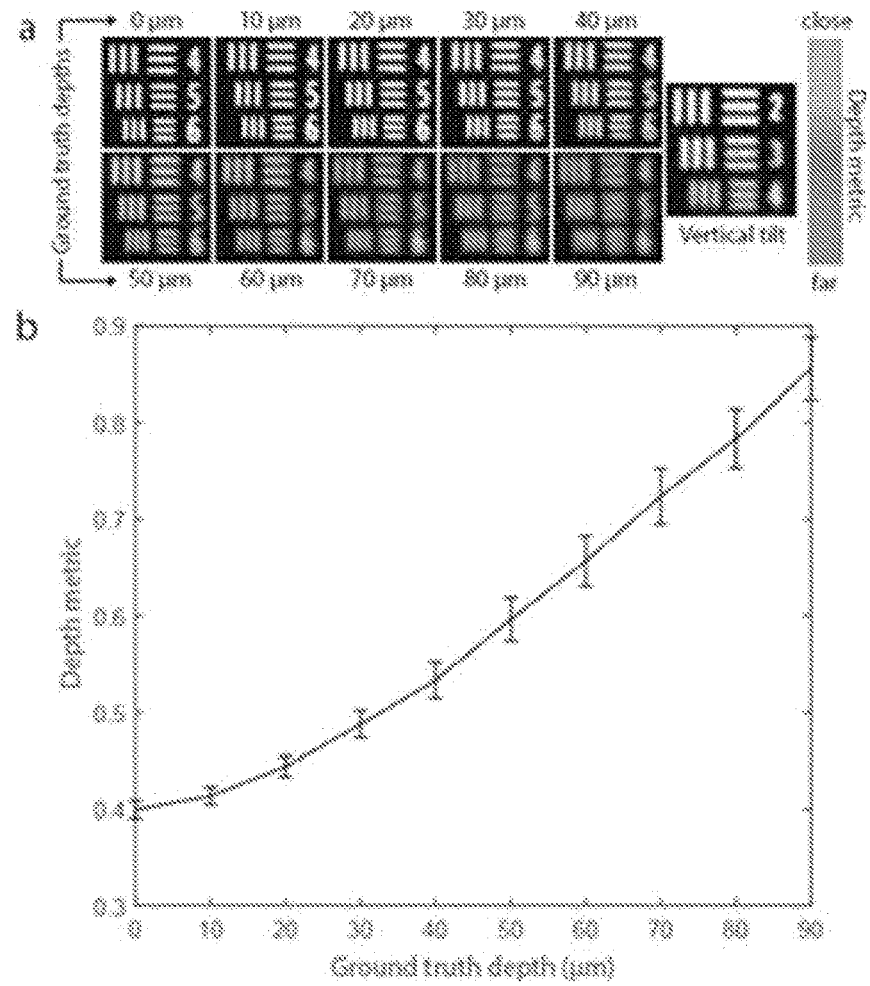
FIG. 12a represents a depth map for a series of images of the USAF target (group 5), generated using an embodiment of the present invention.
FIG. 12b is a plot of a depth metric as a function of the known ground truth depth (MOF fiber facet to USAF target distance) to the target used to generate this embodiment.

The entire dataset in FIG. 12*a* is processed together so that the constant Δz is the same for each image. As expected, the hue-coded depth metric d indicates that the USAF target is moved farther from the fiber facet as the ground truth (applied via a manual micrometer stage) increases from 0 to 90 μm. When a vertical tilt is applied to the USAF target, the depth variation can clearly be seen in the hue-coded image where the top is closer to the fiber facet than the bottom. As a result of the aperture/focus approximation, the relationship between the depth metric is slightly nonlinear, especially at small distances, as shown in FIG. 12(*b*). Nevertheless, useful 3D information can still be obtained such as relative depth ordering of objects in the scene. If need be, depth values could be rescaled to their true values via a calibrated look up table from measurements of a test object at known distances.

Another popular application of light field imaging is synthetic refocusing. The data contained in the light field allows for reorganization of the spatio-angular structure of light in order to digitally change the focus of an image after capture. This is mostly easily understood by first taking images of a 3D scene at all viewpoints in (u,v) space. To create a synthetically refocused image at a given depth, one first needs to correct for the parallax that would be incurred for an object at each viewpoint at said depth. This amounts to a translational shift of the image in (x,y) space that is proportional to the (u,v) vector describing the viewpoint coordinate. Once this parallax is accounted for, the shifted images are summed to create the synthetically refocused image (this is sometimes called the "shift and add" technique). Despite the aperture-focus approximation, synthetic refocusing is possible with the light field estimates obtained from MOF images using embodiments of the present invention.

Figure 13:
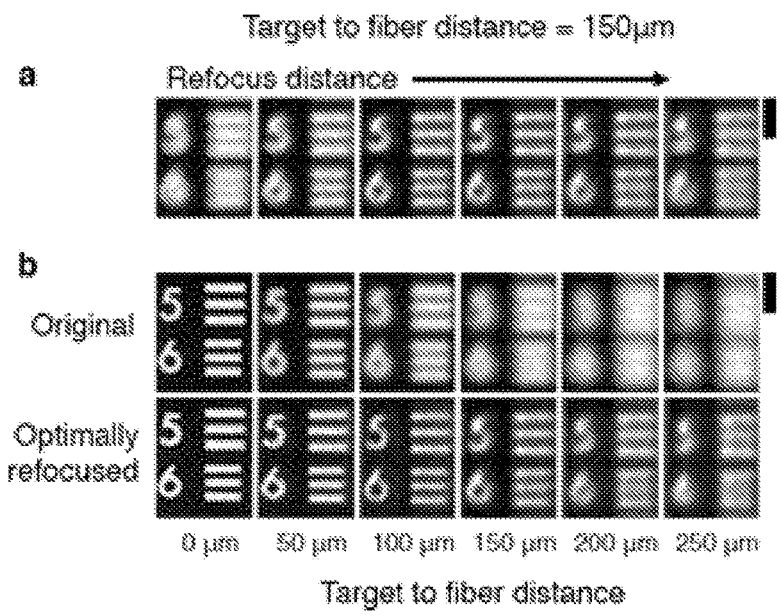
FIGS. 13a and 13b illustrate results of computational refocusing of a USAF target image at various distances.

FIG. 13*a* shows a USAF target image at 150 μm, refocused at various distances, increasing from left to right. The light field estimate L is then computationally refocused to successively larger distances from the fiber facet (images are ordered left-close to right-far). The initially out-of-focus image (far left panel (13*a*)) converges to a focus (middle panel (13*a*)) before blurring after over-focusing (far right panel (13*a*)). Synthetic refocusing was then tested for a range of fiber facet to target distances. FIG. 13*b* shows in the top row the original images of the USAF target at distances of 0-250 μm (Scalebars: 100 μm). The bottom row shows the sharpest synthetically refocused image as judged by eye for each distance. Note that here the refocusing is achieved after image capture and therefore the target is not moved in order to achieve the effect. This result is purely computational. Also note that the discrepancy between the far left image in FIG. 13*a* and the "original" 150 μm image in FIG. 13*b* is due to the Gaussian light field model used to construct the light field estimate. FIG. 13*a* comes from this light field estimate, whereas the "original" images in FIG. 13*b* are obtained prior to without the light field estimate since they do not require light field data. Clear sharpening can be seen upon synthetic refocusing for 50 μm and 100 μm distance images. It may be argued that these may be obtained via judicious deconvolution or unsharp masking. However, the latter cannot be said for the 150-250 μm refocused images, where grating lines that are completely blurred in the original images are rendered resolvable in the optimally refocused images.

As noted above, with the images provided by way of the present invention, various approaches for 3D visualisation of objects. For example, a scene's 3D structure can be directly observed by stereo images such as stereographs and stereo anaglyphs (eg. through red-cyan stereo glasses or VR goggle devices) and perspective shifting (parallax) animations. Alternatively, depth mapping techniques can be applied, eg. with depth maps constructed by a maximum intensity projection of a deconvolved light field focal stack.

As can be seen from the foregoing the image processing methods described herein enable MOFs to be used as light field imaging elements. Use of an MOF for light field imaging enables the use of significantly slimmer endoscopes than existing rigid stereo endomicroendoscopes, which rely on a pair of separated optical imaging paths to record stereo data.

Moreover conveniently, preferred forms of the techniques disclosed herein do not require any hardware modifications to MOF-based systems, as all of the data required for light field estimation is contained within the individual cores.

Trials involving imaging of scattering animal tissue using the present invention in cellular structures (in particular, a 5 mm slice of mouse brain stained with proflavine, imaged through a fiber bundle) have shown very good quantitative agreement between the proflavine depth distribution as measured by the light field approach in accordance with the invention and that obtained with a benchtop confocal microscope.

Figure 14:
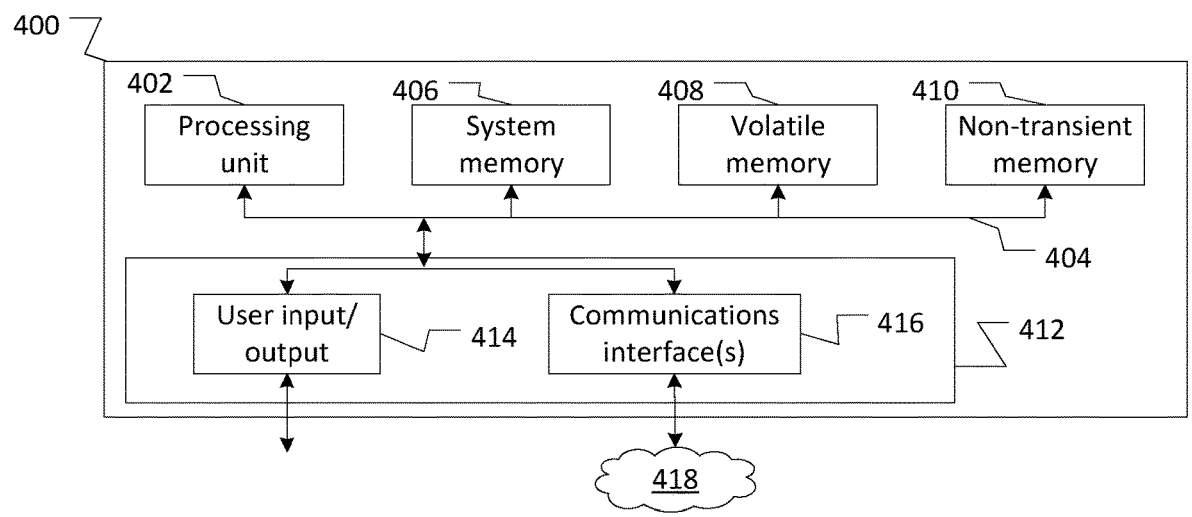
FIG. 14 is a block diagram illustrating a computer processing system suitable for use as an image processing system for processing images captured by way of the system of FIG. 2.

FIG. 14 is a block diagram illustrating a typical computer processing system 400 suitable for use/configuration as an image processing system for processing images captured by camera CAM in the system of FIG. 2 according to any of the various aspects and embodiments described herein. The image processing system may be a separate computing system (perhaps located remotely to the imaging components) or may form part of a control system for the MOF imaging system.

Computer processing system 400 comprises a processing unit 402. The processing unit 402 may comprise a single computer-processing device (e.g. a central processing unit, graphics processing unit, or other computational device), or may comprise a plurality of computer processing devices. In some instances processing is performed solely by processing unit 402, however in other instances processing may also, or alternatively, be performed by remote processing devices accessible and useable (either in a shared or dedicated manner) by the computer processing system 400.

Through a communications bus 404 the processing unit 402 is in data communication with one or more machine-readable storage (memory) devices that store instructions and/or data for controlling operation of the computer processing system 400. In this instance computer processing system 400 comprises a system memory 406 (e.g. a BIOS or flash memory), volatile memory 408 (e.g. random access memory such as one or more DRAM modules), and non-volatile/non-transient memory 410 (e.g. one or more hard disk or solid state drives).

Computer processing system 400 also comprises one or more interfaces, indicated generally by 412, via which the computer processing system 400 interfaces with various components, other devices and/or networks. Other components/devices may be physically integrated with the computer processing system 400, or may be physically separate. Where such devices are physically separate connection with the computer processing system 400 may be via wired or wireless hardware and communication protocols, and may be direct or indirect (e.g., networked) connections.

Wired connection with other devices/networks may be by any standard or proprietary hardware and connectivity protocols. For example, the computer processing system 400 may be configured for wired connection with other devices/communications networks by one or more of: USB; FireWire; eSATA; Thunderbolt; Ethernet; Parallel; Serial; HDMI; DVI; VGA; AudioPort. Other wired connections are possible.

Wireless connection with other devices/networks may similarly be by any standard or proprietary hardware and communications protocols. For example, the computer processing system 400 may be configured for wireless connection with other devices/communications networks using one or more of: infrared; Bluetooth (including early versions of Bluetooth, Bluetooth 4.0/4.1/4.2 (also known as Bluetooth low energy) and future Bluetooth versions); Wi-Fi; near field communications (NFC); Global System for Mobile Communications (GSM), Enhanced Data GSM Environment (EDGE), long term evolution (LTE), wideband code division multiple access (W-CDMA), code division multiple access (CDMA). Other wireless connections are possible.

Generally speaking, the devices to which computer processing system 400 connects—whether by wired or wireless means—allow data to be input into/received by computer processing system 400 for processing by the processing unit 402, and data to be output by computer processing system 400. Example devices are described below, however it will be appreciated that not all computer processing systems will comprise all mentioned devices, and that additional and alternative devices to those mentioned may well be used.

For example, computer processing system 400 may comprise or connect to one or more input devices by which information/data is input into (received by) the computer processing system 400. Such input devices may comprise physical buttons, alphanumeric input devices (e.g., keyboards), pointing devices (e.g., mice, track-pads and the like), touchscreens, touchscreen displays, microphones, accelerometers, proximity sensors, GPS devices and the like. Computer processing system 400 may also comprise or connect to one or more output devices 414 controlled by computer processing system 400 to output information. Such output devices may comprise devices such as indicators (e.g., LED, LCD or other lights), displays (e.g., LCD displays, LED displays, plasma displays, touch screen displays), audio output devices such as speakers, vibration modules, and other output devices. Computer processing system 400 may also comprise or connect to devices capable of being both input and output devices, for example memory devices (hard drives, solid state drives, disk drives, compact flash cards, SD cards and the like) which computer processing system 400 can read data from and/or write data to, and touch-screen displays which can both display (output) data and receive touch signals (input).

Computer processing system 400 may also connect to communications networks (e.g. the Internet, a local area network, a wide area network, a personal hotspot etc.) to communicate data to and receive data from networked devices, which may be other computer processing systems.

The architecture depicted in FIG. 14 may be implemented in a variety of computer processing systems, for example a laptop computer, a netbook computer, a tablet computer, a smart phone, a desktop computer, a server computer. It will also be appreciated that FIG. 14 does not illustrate all functional or physical components of a computer processing system. For example, no power supply or power supply interface has been depicted, however computer processing system 400 will carry a power supply (e.g. a battery) and/or be connectable to a power supply. It will further be appreciated that the particular type of computer processing system will determine the appropriate hardware and architecture, and alternative computer processing systems may have additional, alternative, or fewer components than those depicted, combine two or more components, and/or have a different configuration or arrangement of components.

Operation of the computer processing system 400 is also caused by one or more computer program modules which configure computer processing system 400 to receive, process, and output data.

As used herein, the term "module" to refers to computer program instruction and other logic for providing a specified functionality. A module can be implemented in hardware, firmware, and/or software. A module is typically stored on the storage device 408, loaded into the memory 406, and executed by the processor 402.

A module can include one or more processes, and/or be provided by only part of a process. Embodiments described herein can include other and/or different modules than the ones described here. In addition, the functionality attributed to the modules can be performed by other or different modules in other embodiments. Moreover, this description occasionally omits the term "module" for purposes of clarity and convenience.

It will be appreciated that the types of computer systems 400 used may vary depending upon the embodiment and the processing power used by the entity. For example, the server systems may comprise multiple blade servers working together to provide the functionality described herein.

As will be appreciated, the approach of the present invention is camera frame rate-limited, does not require calibration and is not perturbed by moderate fiber bending, meaning it is suitable for potential clinical applications.

Other incoherent imagine modalities such as brightfield imaging are also amenable to this approach, and it can also be used with fiber bundles employing digital lenses.

As discussed above, embodiments of the present invention concern the relationship between the intra-core intensity patterns and the angular dimension of the light field incident on the distal end of the fiber bundle. The analysis included in the Annex A provides a quantification of this relationship.

Key to this relationship is the fact that the normal LMI equation (Eq. 2 above) is modified for application to pairs of images at the same focus position but with different collection apertures. This arises because the centroid shift (stereo disparity, or lateral shift) of a point source is not linear in z, as would be the case with a standard light field.

Whilst the above disclosure concerns embodiments of the invention that generate or modify an image using a "simulated aperture" technique applied to the fiber cores, it will be appreciated that other methods of processing or analysing the image intensity patterns across each core—in order to extract the light field angular information for that core—may be used. For example, a pattern matching algorithm may be applied, comparing the image intensity pattern with stored patterns, generated for the MOF by way of a pattern calibration process. The calibration process involves obtaining a reference image for a point source at each of a plurality of angles. These reference images are then used to generate the stored patterns for each core, against which received images can be compared using standard computational pattern matching algorithms.

It will be understood that the invention disclosed and defined in this specification extends to all alternative combinations of two or more of the individual features mentioned or evident from the text or drawings. All of these different combinations constitute various alternative aspects of the invention.

ANNEX A

Principle of Operation

Consider a point source imaged through an optical fiber bundle, a distance z from the fiber facet. A light ray at angle θ from the meets the fiber facet at position x,y from the centerline of the fiber bundle, $\theta_x$ and $\theta_y$ being the angles of inclination of rays from the yz and xz planes, respectively.

To illustrate this, the raw output image of a fluorescent bead at an axial distance of z=26 μm as received at the proximal end of the fiber bundle is shown in FIG. 15a (scale bar 5 μm). A radially symmetric pattern of fiber modes is visible due to the relationship between modal coupling efficiency and input ray angle θ. The fiber bundle used in this work has an outer diameter of 750 μm and contains ~30,000 substantially circular cores with 3.2 μm average center-to-center spacing, average core radius a=1 μm, and a numerical aperture (NA) of 0.39.

On average, each core in this fiber bundle supports approximately $$\left(\frac{2\pi}{\lambda}aNA\right)^2 \bigg/ 2 \approx 10$$

modes at λ=550 nm (24).

Figure 15:
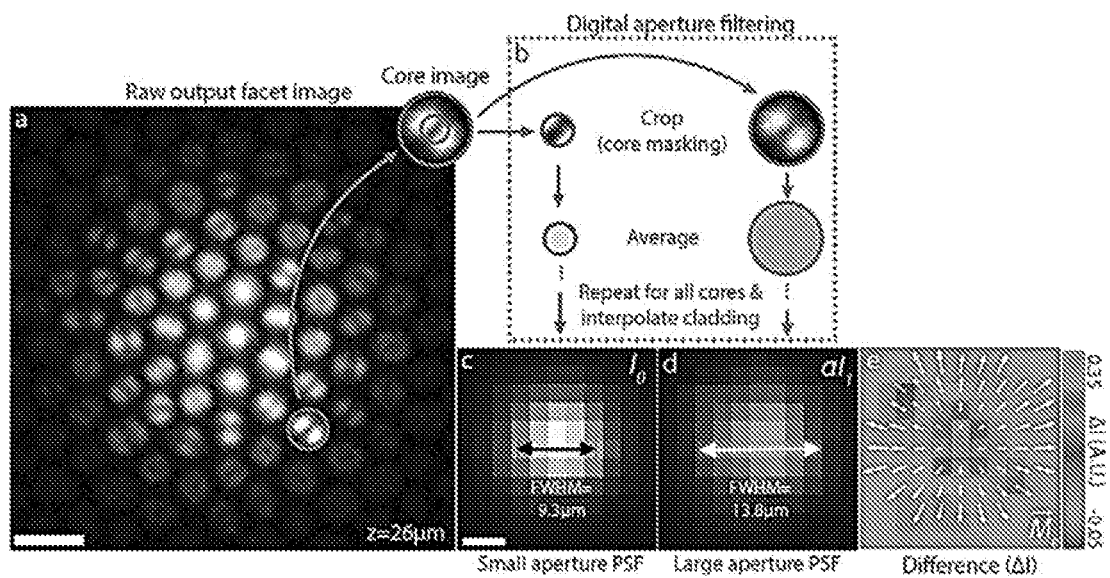
FIG. 15 illustrates application of light moment imaging (LMI) to a MOF image processed in accordance with an embodiment of the invention.

As discussed elsewhere in this specification, post processing of the image data allows digital manipulation of the fiber's numerical aperture (NA). This relies on the fact that the higher order modes, which are preferentially excited at larger angles of incidence, carry more energy near the core/cladding interface than the lower order modes. Light is effectively pushed towards the edge of each core with increasing ray angle. By the digital aperture filtering approach of embodiments of the invention (selectively removing light near the periphery of each core) a synthetically constricted NA is achieved. This is illustrated in FIG. 15, in particular 15c and 15d.

The full orientation of input light cannot be ascertained from this observation alone, due to azimuthal degeneracies of the core's modes. To address this, LMI is applied. In LMI, a continuity equation describing conservation of energy between two image planes can be used to calculate the average ray direction (represented by the light field moment vector $\vec{M}=[M_x, M_y]$) at a given point in the image I:

$$\partial I/\partial z = -\nabla_\perp \cdot I\vec{M} \tag{4}$$

where $$\nabla_\perp = \left[\frac{\partial}{\partial x}, \frac{\partial}{\partial y}\right].$$

From this information, a light field L(x,y,u,v) can be constructed assuming a Gaussian distribution in (angular) uv space around this average ray angle:

$$L(x,y,u,v)=I(x,y)\times\exp[-2(u-M_x)^2/\sigma^{-2}-2(v-M_y)^2/\sigma^{-2}] \tag{5}$$

Here, angular ray space is parametrized by u=tan $\theta_x$ and v=tan $\theta_y$, where tan $\theta_{x,y}$ relate to the angles of inclination of rays from the yz and xz planes, respectively. In this notation, $\vec{M}=[\int Lududv, \int Lvdudv]/\int Ldudv$, and $\sigma$ is an adjustable parameter discussed below. This Gaussian assumption is based on the fact that a finely spatially sampled light field loses all structure in the angular domain, similar to a Shack-Hartmann wavefront sensor. The resulting light field reveals depth information via lateral motion of objects when changing viewpoint, and can be processed into stereographs, full-parallax animations, refocused images and depth maps.

Conventional LMI (Eq. 6) requires a pair of input images at different focus positions. However, fine focus control is not available on most microendoscopes, and even if it were, traditional LMI is not single-shot. Instead, it is necessary to modify Eq. 4 so that it can be used with pairs of images at the same focus position but with different collection apertures.

Imaging Model

Considering the point source a distance z from the bare fiber facet, this source is out of focus since there is no imaging lens on the fiber facet. Thus, the apparent size of the point source as viewed from the output facet will grow with increasing acceptance angle (i.e. NA) of the fiber. When the fiber NA is computationally reduced from a large (full) aperture (regions shown at right side of FIG. 15b) to a smaller aperture (regions shown at left side of FIG. 15b) by core masking, the width of the point-spread function (PSF) also decreases (FIGS. 15c,d) due to the increased depth of field.

In FIG. 15b, the right and left circles indicate example averaging regions for large (full) and small aperture images, respectively. Large aperture images are created by averaging the entire region for each core and then filling in the remaining areas (interstitial regions) by linear interpolation. Small aperture images are created in the same way, with an average taken over the smaller region, as depicted on the left hand side of the figure.

FIGS. 15c and 15d show, respectively, the small aperture image ($I_0$) and the large aperture image ($\alpha I_1$) of the fluorescent bead after interpolation. The scaling constant $\alpha$ is chosen such that the total intensities of the two images are equal. The PSF (full width at half maximum, FWHM) for the small and large apertures are indicated in FIGS. 15c and 15d, namely FWHM=9.3 and FWHM=13.8, respectively. FIG. 15e shows the difference between these images, with arrows indicating the effective light field moment vector field $\vec{M}_e$.

The PSF of the system is modelled as a 2D Gaussian with width proportional to tan θ (30), where θ is the maximum ray angle collected by the fiber (to be computationally adjusted post-capture):

$$PSF(\vec{r}, z, \tan\theta) = \frac{1}{z^2}\exp[-4\ln(2)|\vec{r}|^2/z^2\tan^2\theta] \quad (6)$$

By considering a collection of j point sources, the following modified LMI equation is arrived at, that depends on two images, $I_0$ and $I_1$, with maximum collection angles (apertures) $\theta_0$ and $\theta_1$:

$$I_0 - \alpha I_1 = -\left(\frac{\tan\theta_1}{\tan\theta_0} - 1\right)\nabla_\perp \cdot I\vec{M}_e \quad (7)$$

Where $$I = \frac{(I_0 + \alpha I_1)}{2},$$

$\vec{M}_e = \Sigma_{j=1}^n z_j B_j PSF_j \vec{M}_j/I$ is the effective light field moment vector, $z_j$ is the depth of point source j, $B_j PSF_j$ is the intensity at position (x,y) due to point source j, and $$\alpha = \int I_0 d\vec{r} / \int I_1 d\vec{r} = \left(\frac{\tan\theta_1}{\tan\theta_0}\right)^2.$$

Equation 6 is convenient since it is possible to obtain both $I_0$ and $I_1$ in a single shot via digital aperture filtering. It is then possible to solve for $\vec{M}_e$ in the Fourier domain; the resulting $\vec{M}_e$ for a fluorescent bead at z=26 μm is superimposed over the image $\Delta I = I_0 - \alpha I_1$ in FIG. 15e. Finally, a light field is constructed as in Eq. 5, with $\vec{M} \rightarrow \vec{M}_e$. This $\vec{M} \rightarrow \vec{M}_e$ substitution alters the parallax behaviour of the light field such that the centroid shift $\vec{C}$ of point source is not linear in z, as would be the case with a standard light field:

$$\vec{C} = \frac{z^2 + \sigma_0^2/\tan^2\theta_0}{z^2 + 2\ln(2)h^2 + \sigma_0^2/\tan^2\theta_0}[u, v] \quad (8)$$

where $h \stackrel{\text{def}}{=} \sigma/\tan\theta_0$ is an adjustable reconstruction parameter, and $\sigma_0$ is the full width at half maximum (FWHM) of the PSF at z=0. Tan $\theta_0$, tan $\theta_1$, and $\sigma_0$ are obtained experimentally by fitting a 2D Gaussian to images of isolated beads at a series of depths for large and small apertures.

Figure 16:
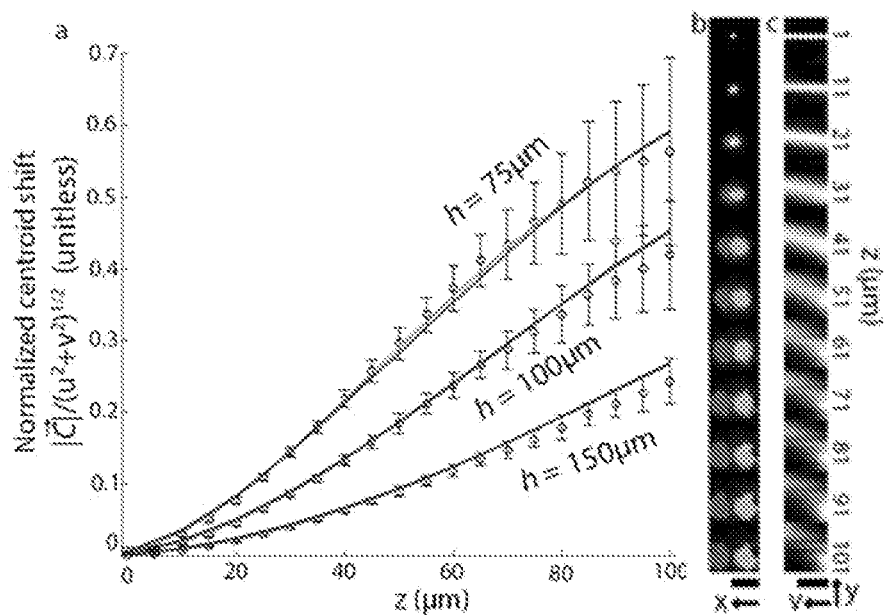
FIG. 16 illustrates the relationship between stereo disparity of a moving viewpoint (increasing axial distance from object) when applying the method of an embodiment of the invention.

FIG. 16a presents the quantification of disparity, ie. the fluorescent bead centroid shift (disparity) as a function of bead depth z for h=75, 100 and 150 μm. In particular, the figure shows experimentally measured $|\vec{C}|$ values for fluorescent beads at 1-101 μm from the fiber facet, along with simulated and theoretical results. Centroid shift corresponds to the magnitude of the centroid shift in xy-space $|\vec{C}|$ per unit displacement in uv-space. Datapoints are experimentally measured values and error bars represent the standard deviation over 5 beads.

As can be seen, both simulation and theory show very good agreement with experimental data for a range of h values (for each h value, the two curves show respectively theoretical—based on Eq. 8—and simulated centroid shifts). The theoretical curves use known physical (z, tan $\theta_0$) and reconstruction quantities (u, v, h)—no fitting parameters are used.

FIG. 16b illustrates the lateral shift of a fluorescent bead as a function of bead depth, namely the extreme left- and right-viewpoint images of fluorescent beads at increasing depths (colour viewing allows 3D imaging viewable with red-cyan stereo glasses, where red is represented in the figure as dark grey (left) and cyan is represented as light grey (right); Scalebar 25 μm), while FIG. 16c shows the characteristic slanted lines of point sources at different depths in the epipolar plane, ie. a central yv slice (x=0,u=0) of the light field for each bead depth (Scalebar 25 μm).

The invention claimed is:
1. A method for generating one or more images from light received by an imager via a multiplicity of waveguides, the light generated from a light field incident on said multiplicity of waveguides, the method including:

receiving a digital image containing a plurality of pixels, the digital image including a plurality of regions, each of said regions corresponding to a waveguide core and including a plurality of pixels;

processing an image intensity pattern across each of said regions to determine a light field angular dimension measure for that region;

applying the angular dimension measure to one or more of the pixels included in each region to produce one or more sets of modified image data;

using the one or more sets of modified image data to generate one or more images.

2. An imaging system comprising:

a multicore optical fiber (MOF) extending from a proximal end to a distal end;

a light source for illuminating a scene at the distal end of the MOF;

an imager arranged with respect to the proximal end of the MOF to capture an image of light propagated along the MOF;

a data processing system configured to receive images captured by the imager and configured to execute instructions that cause the data processing system to perform a method as claimed in claim 1.

3. The imaging system of claim 2, wherein the MOF comprises an endoscope.

4. An image processing system comprising at least one processing unit and at least one memory for storing instructions for execution by the at least one processing unit, the instruction being executed to perform a method as claimed in claim 1.

5. The method of claim 1, wherein the processing of the image intensity pattern across each of said regions includes analyzing each region by way of a simulated aperture technique involving, for each region, a computational comparison of image intensity under a first computational aperture with image intensity under a second computational aperture.

6. The method of claim 5, wherein pixels in one of said first and second computational apertures comprise a subset of pixels in the other of said first and second computational apertures.

7. The method of claim 5, wherein a set of pixels in each computational aperture are different, selected in accordance with the particular light field angular dimension measure to be extracted from the processing step.

* * * * *